(12) United States Patent
Unger et al.

(10) Patent No.: US 11,304,899 B2
(45) Date of Patent: Apr. 19, 2022

(54) COMPOSITIONS OF FLUOROCARBON NANOEMULSION, AND METHODS OF PREPARATION AND USE THEREOF

(71) Applicants: NuvOx Pharma LLC, Tucson, AZ (US); Evan C. Unger, Tucson, AZ (US)

(72) Inventors: Evan C. Unger, Tucson, AZ (US); Edmund R. Marinelli, Tucson, AZ (US)

(73) Assignee: NuvOx Pharma LLC, Tucson, AZ (US)

( * ) Notice: Subject to any disclaimer, the term of this patent is extended or adjusted under 35 U.S.C. 154(b) by 0 days.

(21) Appl. No.: 16/060,950

(22) PCT Filed: Dec. 20, 2016

(86) PCT No.: PCT/US2016/067650
§ 371 (c)(1),
(2) Date: Jun. 10, 2018

(87) PCT Pub. No.: WO2017/112614
PCT Pub. Date: Jun. 29, 2017

(65) Prior Publication Data
US 2018/0360754 A1    Dec. 20, 2018

Related U.S. Application Data

(60) Provisional application No. 62/270,226, filed on Dec. 21, 2015.

(51) Int. Cl.
| | | |
|---|---|---|
| *A61K 9/107* | (2006.01) | |
| *A61K 47/24* | (2006.01) | |
| *A61K 47/06* | (2006.01) | |
| *A61K 31/02* | (2006.01) | |
| *A61K 47/02* | (2006.01) | |
| *A61K 47/10* | (2017.01) | |
| *A61K 47/69* | (2017.01) | |
| *B82Y 5/00* | (2011.01) | |
| *C08L 27/12* | (2006.01) | |

(52) U.S. Cl.
CPC ............ *A61K 9/1075* (2013.01); *A61K 31/02* (2013.01); *A61K 47/02* (2013.01); *A61K 47/06* (2013.01); *A61K 47/10* (2013.01); *A61K 47/24* (2013.01); *A61K 47/6907* (2017.08); *A61K 47/6935* (2017.08); *B82Y 5/00* (2013.01); *C08L 27/12* (2013.01)

(58) Field of Classification Search
None
See application file for complete search history.

(56) References Cited

U.S. PATENT DOCUMENTS

| | | | | |
|---|---|---|---|---|
| 2013/0022550 A1* | 1/2013 | Unger | ................. | A61K 49/223 424/9.52 |
| 2014/0004099 A1* | 1/2014 | Culp | ..................... | A61K 45/06 424/94.64 |

FOREIGN PATENT DOCUMENTS

| | | |
|---|---|---|
| EP | 1323434 A2 | 7/2003 |
| WO | 2013013067 A2 | 1/2013 |
| WO | 2015134735 A1 | 9/2015 |
| WO | 2015192093 A1 | 12/2015 |

OTHER PUBLICATIONS

Density of aqueous solutions of organic substances as sugars and alcohols, The Engineering ToolBox, available at https://www.engineeringtoolbox.com/density-aqueous-solution-organic-sugar-alcohol-concentration-d_1954.html, accessed Apr. 3, 2020.*
Fernandes, D.A., et al., Multifunctional perfluorocarbon nanoemulsions for cancer therapy and imaging, Proc. of SPIE vol. 9338 93380R-1 (2015), doi: 10.1117/12.2079914.*
EP 16879945.0, Extended European Search Report, dated Sep. 20, 2019.

* cited by examiner

*Primary Examiner* — H. Sarah Park
(74) *Attorney, Agent, or Firm* — Milstein Zhang & Wu LLC

(57) ABSTRACT

The invention provides novel compositions of fluorocarbon nanoemulsions comprising one or more of fluorosurfactants and phospholipids, and methods of preparation and use thereof for enhanced oxygen delivery.

4 Claims, 10 Drawing Sheets

COMPOSITIONS OF FLUOROCARBON NANOEMULSION, AND METHODS OF PREPARATION AND USE THEREOF

PRIORITY CLAIMS AND RELATED PATENT APPLICATIONS

This application is the U.S. national phase of and claims priority to PCT/US16/67650, filed Dec. 20, 2016, which claims the benefit of priority to U.S. Provisional Application Ser. No. 62/270,226, filed on Dec. 21, 2015, the entire content of which is incorporated herein by reference in its entirety.

TECHNICAL FIELDS OF THE INVENTION

This invention generally relates to compositions of fluorocarbon nanoemulsions and methods of their preparation and use. More particularly, the invention relates to unique fluorocarbon nanoemulsions stabilized with one or more of perfluoro-n-hexyl-oligoethyleneoxy-alcohols and phospholipids, and methods of preparation and application thereof.

BACKGROUND OF THE INVENTION

Common surgical and interventional procedures as well as trauma and natural disease states may lead to blood loss, ischemia or hypoxia, which if not treated timely and properly can cause organ and tissue damage resulting in morbidity and mortality. Blood loss episodes present as ischemic syndromes widely distributed throughout the body and extremities and in the brain as strokes. Prompt revascularization and restoration of oxygenated blood flow remain the emphases of clinical stroke therapy. Additionally, donated blood appears to be in constant shortage partly due to the limited shelf life of donated blood and it is prone to viral contamination. Oxygen carriers or artificial blood are useful in helping with treatment of various diseases and conditions including in radiotherapy and chemotherapy.

Emulsified fluorocarbon (FC)-based oxygen carriers have been reported, for example, utilizing higher molecular weight fluorocarbons (e.g., perfluorodecalin and perfluorooctylbromide). These compositions, however, have largely failed to meet the rigorous clinical requirements and many challenges remain to address the urgent needs for safe, reliable and effective oxygen carriers.

SUMMARY OF THE INVENTION

The present invention is based in part of the unexpected discovery that fluorocarbon nanoemulsions uniquely formulated with surfactants or stabilizing agents selected from perfluoro-n-hexyl-oligoethyleneoxy-alcohols, phospholipids or combinations thereof, resolve the critical issues of bioaccumulation of metabolites and degradation products, which form from fluorosurfactants with perfluoroalkyl groups of more than 6 fully fluorinated carbons.

Fluorocarbon nanoemulsions of the invention derive a significant benefit from employing a shorter perfluorocarbon chain of the surfactant because excretion and metabolism products do not bioaccumulate as do those with larger perfluoroalkyl moieties.

In one aspect, the invention generally relates to a composition of a fluorocarbon nanoemulsion that includes a fluorocarbon ranging from about 4 to about 8 carbons; and one or more surfactants selected from perfluoro-n-hexyl-oligoethyleneoxy-alcohols, phospholipids or combinations thereof. In certain embodiments, the one or more surfactants comprise a perfluoro-n-hexyl-oligoethyleneoxy-alcohol and/or a mixture of three phospholipids.

In yet another aspect, the invention generally relates to a method for forming a nanoemulsion. The method includes: preparing an aqueous first mixture comprising PEG Telomer B and a fluorocarbon; transferring via a homogenizer comprising a bypass valve and a pneumatic unit the first mixture between a first container and a second container and back to the first container, wherein the bypass valve is open; initiating the pneumatic unit using a closed bypass valve to form a homogenized primary nanoemulsion; disposing the homogenized primary nanoemulsion into an aqueous solution of sucrose or another viscogen and optionally one or more of pharmaceutically acceptable buffer salts and microbiocidal agents, disposed in a first pressure vessel to form a second mixture; attaching the first pressure vessel to an input end of the homogenizer; attaching a second pressure vessel to an output end of the homogenizer; operating the pneumatic unit with the bypass valve closed to form nanoemulsion until all of the second mixture is transferred to the second pressure vessel; and pressurizing the second pressure vessel to transfer and sterilize the nanoemulsion through a 0.8/0.2 micron filter and into a third pressure vessel.

In yet another aspect, the invention generally relates to a method for forming a nanoemulsion. The method includes: preparing an aqueous first mixture comprising one or more perfluoro-n-hexyl-oligoethyleneoxy-alcohols where the oligoethyleneoxy moieties are from 1 to 16 units in length, and a fluorocarbon; transferring via a homogenizer comprising a bypass valve and a pneumatic unit the first mixture between a first container and a second container and back to the first container, wherein the bypass valve is open; initiating the pneumatic unit with a closed bypass valve to form a homogenized primary emulsion; disposing the homogenized primary emulsion into a sucrose solution comprising optionally one or more of pharmaceutically acceptable buffer salts, viscogens and microbiocidal agents disposed in a first pressure vessel to form a second mixture; attaching the first pressure vessel to an input end of the homogenizer; attaching a second pressure vessel to an output end of the homogenizer; operating the pneumatic unit with the bypass valve closed to form an emulsion until all of the second mixture is transferred to the second pressure vessel; and pressurizing the second pressure vessel to transfer and sterilize the emulsion through a 0.8/0.2 micron filter and into a third pressure vessel.

In yet another aspect, the invention generally relates to a method for forming a nanoemulsion. The method includes: preparing an aqueous first mixture comprising a perfluoro-n-hexyl-oligoethyleneoxy-alcohol, sucrose and optionally one or more of pharmaceutically acceptable buffer salts, viscogens and approved biocidal sterilants; disposing the first mixture into a vial using a syringe and a needle attached to the syringe; adding a fluorocarbon into the vial; stoppering and crimp capping the vial, followed by vortexing and sonicating the vial.

In yet another aspect, the invention generally relates to a method for forming a nanoemulsion. The method includes: forming a mixture comprising one or more phospholipids, water, glycerol, monobasic sodium phosphate and dibasic sodium phosphate; transferring the mixture via a 0.2 micron filter into a sterile vessel; disposing the mixture into a vial; adding a fluorocarbon to the vial and immediately stoppering and crimp capping the vial, followed by vortexing and sonicating the vial.

In yet another aspect, the invention generally relates to a nanoemulsion formed by a method disclosed herein.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF THE INVENTION

Figure 1:
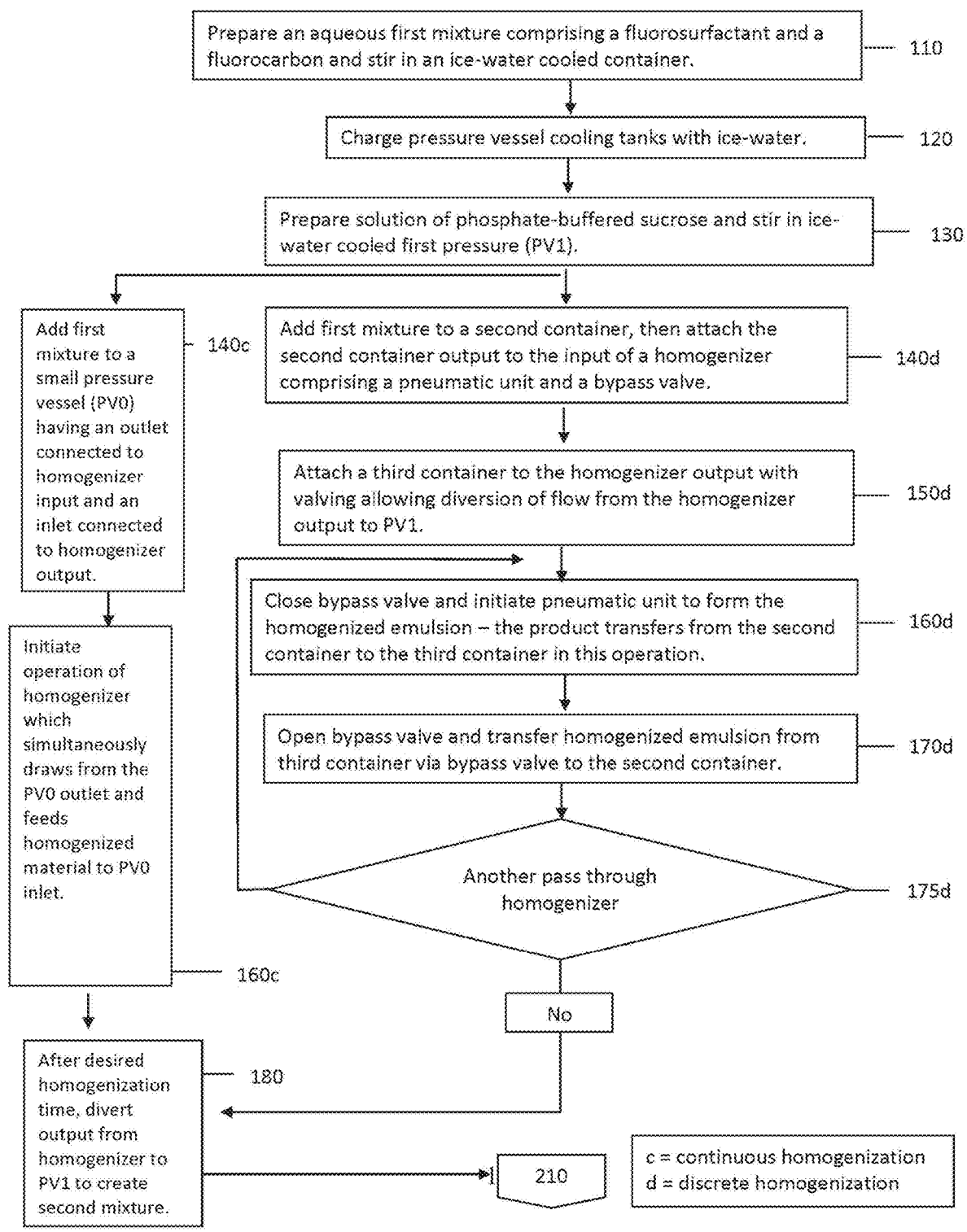
FIG. 1 is a flowchart summarizing an exemplary embodiment of the method according to the invention to generate PEG Telomer B-stabilized perfluorocarbon nanoemulsions by high-pressure homogenization.

The invention provides fluorocarbon nanoemulsions uniquely formulated with surfactants or stabilizing agents selected from perfluoro-n-hexyl-oligoethyleneoxy-alcohols and phospholipids. These fluorocarbon nanoemulsions resolve key issues faced by conventional fluorocarbons-based artificial oxygen carriers, including bioaccumulation of metabolites and degradation products. These undesirable impurities form from fluorosurfactants with perfluoroalkyl groups of more than 6 fully fluorinated carbons and have led to continued setbacks in light of the stringent regulatory standards. Fluorocarbon nanoemulsions of the invention derive a significant benefit from using a shorter perfluorocarbon chain of the surfactant because excretion and metabolism products do not bioaccumulate as do those with larger perfluoroalkyl moieties.

In one aspect, the invention generally relates to a composition of a fluorocarbon nanoemulsion that includes a fluorocarbon ranging from about 4 to about 8 carbons; and one or more surfactants selected from perfluoro-n-hexyl-oligoethyleneoxy-alcohols and phospholipids.

In certain embodiments, the fluorocarbon comprises perfluorobutane, perfluoropentane, perfluorohexane, perfluoroheptane, perfluorooctane, or a mixture of two of more thereof.

In certain preferred embodiments, the fluorocarbon comprises perfluoropentane.

In certain embodiments, the one or more surfactants comprise a perfluoro-n-hexyl-oligoethyleneoxy-alcohol and/or a mixture of three phospholipids.

For example, the perfluoro-n-hexyl-oligoethyleneoxy-alcohol comprises one or more of:

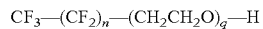

wherein n is 5 and q is an integer from 1 to about 50.

In certain preferred embodiments, the perfluoro-n-hexyl-oligoethyleneoxy-alcohol is

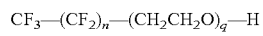

wherein n is 5, and q is an integer from 1 to about 16 (e.g., from about 3 to about 16, from about 6 to about 16, from about 10 to about 16, from about 3 to about 10).

Fluorocarbon may account for any suitable weight percentage in the nanoemulsion, for example, from about 1% to about 50% (e.g., from about 1% to about 40%, from about 1% to about 30%, from about 1% to about 20%, from about 1% to about 10%, from about 1% to about 5%).

Perfluoro-n-hexyl-oligoethyleneoxy-alcohol may account for any suitable weight percentage in the nanoemulsion, for example, from about 0.10% to about 7.5% (e.g., from about 0.10% to about 5%, from about 0.10% to about 4%, from about 0.10% to about 3%, from about 0.10% to about 1.5%).

The phospholipids have any suitable carbon chain length, for example, ranging from about 12 carbons to about 18 carbons (e.g., 12, 13, 14, 15, 16, 17, 18) in length.

The phospholipids may account for any suitable weight percentage in the nanoemulsion, for example, from about 0.10% to about 7.5% (e.g., from about 0.10% to about 5%, from about 0.10% to about 4%, from about 0.10% to about 3%, from about 0.10% to about 1.5%).

The disclosure of PCT/US15/35681, titled "Phospholipid Composition And Microbubbles and Emulsions Formed Using Same" and filed Jun. 12, 2015, is expressly incorporated herein by reference for all purposes.

In certain embodiments where the composition comprises a mixture of three phospholipids, exemplary phospholipids and relative amounts there of may be, for example, from about 75 to about 87 mole % phosphatidylcholine, about 5 to about 15 mole % phosphatidylethanolamine and about 3 to about 20 mole % phosphatidylethanolamine-MPEG, wherein "MPEG" refers to a PEG group having a terminus methoxy group. The MPEG herein may have a molecular weight from about 350 to about 5,000 (e.g., from about 350 to about 4,000, from about 350 to about 3,000, from about 350 to about 2,000, from about 500 to about 5,000, from about 1,000 to about 5,000, from about 1,500 to about 5,000, from about 2,000 to about 5,000, from about 3,000 to about 5,000, from about 4,000 to about 5,000). Phosphatidylethanolamine-PEG, where the oligoethyleneoxy portion of the molecule is terminated with a hydroxyl group as opposed to the methoxy terminus present in MPEG phospholipids can be substituted for the phosphatidylethanolamine-MPEG in the formulation. Combinations of phosphatidylethanolamine-MPEG and phosphatidylethanolamine-PEG may also be employed in any relative ratio, as the oligoethyleneoxy-bearing phospholipid component of these formulations.

In embodiments where the composition comprises a mixture of three phospholipids, exemplary phospholipids and relative amounts there of may be, for example, from about 80 to about 85 mole % phosphatidylcholine, about 8 to about 13 mole % phosphatidylethanolamine and about 6 to about 11 mole % phosphatidylethanolamine-MPEG (or phosphatidylethanolamine-PEG).

In certain embodiments, the phosphatidylethanolamine includes a PEG group with a molecular weight from about 350 to about 5,000 (e.g., from about 350 to about 4,000, from about 350 to about 3,000, from about 350 to about 2,000, from about 500 to about 5,000, from about 1,000 to about 5,000, from about 1,500 to about 5,000, from about 2,000 to about 5,000, from about 3,000 to about 5,000, from about 4,000 to about 5,000).

In certain embodiments, compositions of the invention include PEG Telomer B (PTB) a custom purified medical grade of DuPont Zonyl FS-100 or DuPont FSO. In certain embodiments, compositions of the invention include perfluoro-n-hexyl-oligoethyleneoxy-alcohol. A particular form of perfluoro-n-hexyloligoethyleneoxy-alcohol is a fluorosurfactant product known as DuPont Capstone FS-3100 and, in certain embodiments, compositions of the invention include comprises that material or a custom refined version of that material. In certain embodiments, compositions of the invention include tetradecafluoro-n-hexane (TDFH). In certain embodiments, compositions of the invention include tetradecafluorohexane that may consist of a mixture of 2 or more of its possible structural isomers present in any proportions. In certain embodiments, compositions of the invention include dodecafluoro-n-pentane (DDFP). In certain embodiments, compositions of the invention include dodecafluoropentane that may consist of a mixture of 2 or more of its possible structural isomers present in any proportions.

In certain embodiments, compositions of the invention include one or more of dodecafluoro-n-pentane, 1,2-dipalmitoyl-sn-glycero-3-phosphatidylcholine, 1,2-palmitoyl-sn-glycero-3-phosphoethanolamine-N-[methoxy(polyethylene glycol)-5000] salts such as the sodium salt, and 1,2-dipalmitoyl-sn-glycero-3-phosphoethanolamine.

In certain embodiments, compositions of the invention include one or more of 1,2-dimyristoyl-sn-glycero-3-phosphatidylcholine, 1,2-dimyristoyl-sn-glycero-3-phosphoethanolamine-N-[methoxy(polyethylene glycol)-2000] salts such as the sodium salt, and 1,2-dimyristoyl-sn-glycero-3-phosphoethanolamine. In certain embodiments, compositions of the invention include one or more of 1,2-didodecanoyl-sn-glycero-3-phosphatidylcholine, 1,2-didodecanoyl-sn-glycero-3-phosphoethanolamine-N-[methoxy(polyethylene glycol)-2000] sodium salt, and 1,2-didodecanoyl-sn-glycero-3-phosphoethanolamine.

As aspect of the invention relates a method for preparing perfluorocarbon nanoemulsions. Aqueous mixtures of one or more fluorocarbon surfactants, which have a fluorocarbon moiety comprising only a single chain length, are employed to prepare nanoemulsions of perfluorocarbons. Referring now to FIG. 1, in step (110) the method prepares about a 6% wt/volume mixture of a fluorosurfactant in water for injection (WFI) using a magnetic stirrer in a vessel, disposed in a 2-5° C. bath for a period of between 15 and 60 minutes, while the solution temperature is monitored and maintained at a temperature of 2-5° C.

In certain embodiments, the fluorocarbon of step (110) comprises tetradecafluoro-n-hexane. In certain embodiments, the fluorocarbon of step (110) comprises tetradecafluorohexane which may be a mixture of 2 or more structural isomers. In certain embodiments, the fluorocarbon of step (110) comprises dodecafluoro-n-pentane. In certain embodiments, the fluorocarbon of step (110) comprises dodecafluoropentane which may be a mixture of 2 or more structural isomers.

In certain embodiments, the fluorocarbon of step (110) consists of tetradecafluoro-n-hexane. In certain embodiments, the fluorocarbon of step (110) consists of tetradecafluorohexane. In certain embodiments, the fluorocarbon of step (110) consists of dodecafluoro-n-pentane. In certain embodiments, the fluorocarbon of step (110) consists of dodecafluoropentane.

Further in step (110), method of the invention then quickly adds an aliquot of cold (0-4° C.) perfluorocarbon to the vessel, closes a vessel cap, and then stirs the resulting first mixture for about 1 hour.

In certain embodiments, the fluorocarbon surfactant of step (110) comprises Peg Telomer B (PTB), compound 21,

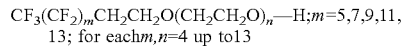

$$CF_3(CF_2)_mCH_2CH_2O(CH_2CH_2O)_n\text{—}H; m=5,7,9,11, 13; \text{for each} m, n=4 \text{ up to} 13 \qquad 21$$

In certain embodiments, the fluorocarbon surfactant of step (110) comprises perfluoro-n-hexyl-oligoethyleneoxy-alcohol. In certain embodiments, the fluorocarbon surfactant of step (110) consists of PEG Telomer B that is the mixture of compounds denoted as 21 above. in certain embodiments, the fluorocarbon surfactant of step (110) consists of perfluoro-n-hexyl-oligoethyleneoxy-alcohol.

In certain embodiments, the fluorosurfactant of step (110) is perfluoro-n-hexyl-oligoethyleneoxy-alcohol surfactant 17, which has an invariant perfluoro-n-hexyl moiety 18, in combination with a variable ethylene oxide moiety 19.

17

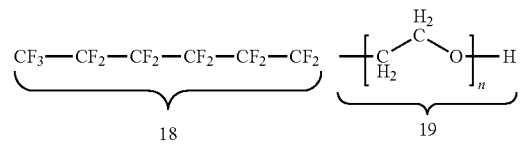

In certain embodiments, the fluorosurfactant of step (110) comprises a perfluoro-n-alkyl-oligoethyleneoxy-alcohol 20 wherein y is greater than 6. In certain embodiments, the fluorosurfactant of step (110) comprises compound 20 wherein y is 7, and wherein n is greater than or equal to 1 and less than or equal to 16.

20 a,b

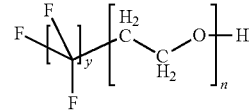

In certain embodiments, the fluorosurfactant of step (110) comprises a perfluoro-n-alkyl-oligoethyleneoxy-alcohol 20a wherein y is 6, and wherein n is greater than or equal to 1 and less than or equal to 16 (e.g., DuPont Capstone FS-3100 fluorosurfactant). In certain embodiments compound 20a can be used as received from the manufacturer. In certain embodiments compound 20a can be subjected to a custom refinement procedure or purification procedure before use.

In certain embodiments, the fluorosurfactant of step (110) comprises compound 20b wherein y is 5, and wherein n is greater than or equal to 1 and less than or equal to 16.

In certain embodiments, the fluorosurfactant of step (110) comprises compound 1. In certain embodiments, the fluorosurfactant of step (110) comprises compound 2. In certain embodiments, the fluorosurfactant of step (110) comprises compound 3. In certain embodiments, the fluorosurfactant of step (110) comprises compound 4. In certain embodiments, the fluorosurfactant of step (110) comprises compound 5. In certain embodiments, the fluorosurfactant of step (110) comprises compound 6. In certain embodiments, the fluorosurfactant of step (110) comprises compound 7. In certain embodiments, the fluorosurfactant of step 110 comprises compound 8. In certain embodiments, the fluorosurfactant of step (110) comprises compound 9. In certain embodiments, the fluorosurfactant of step (110) comprises compound 10. In certain embodiments, the fluorosurfactant of step (110) comprises compound 11. In certain embodiments, the fluorosurfactant of step (110) comprises compound 12. In certain embodiments, the fluorosurfactant of step (110) comprises compound 13. In certain embodiments, the fluorosurfactant of step (110) comprises compound 14. In certain embodiments, the fluorosurfactant of step (110) comprises compound 15. In certain embodiments, the fluorosurfactant of step (110) comprises compound 16.

1

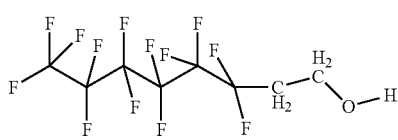

2

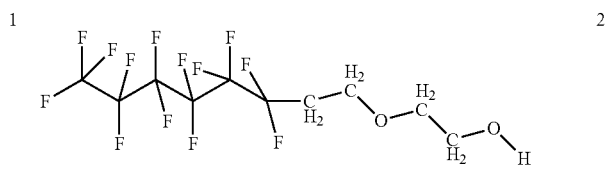

3

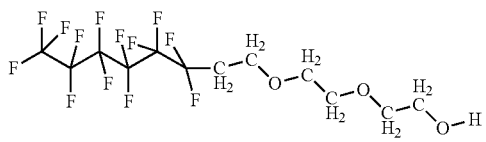

4

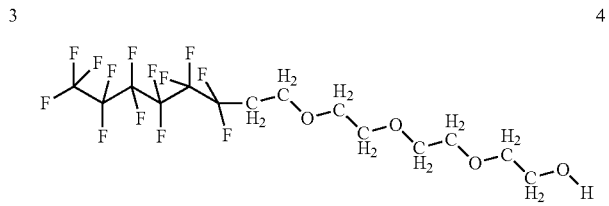

5

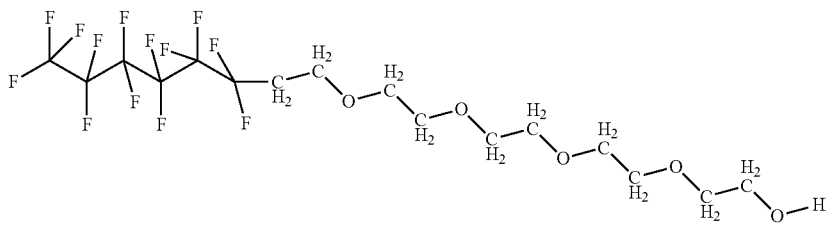

6

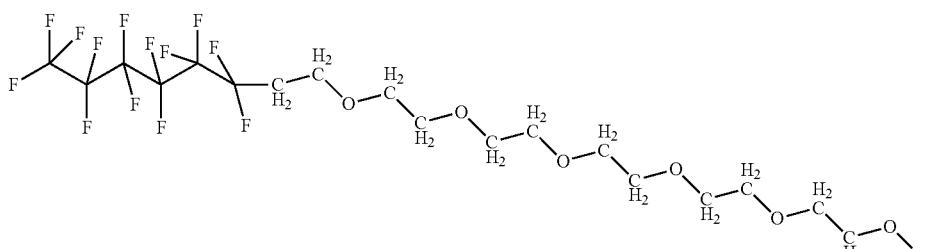

7

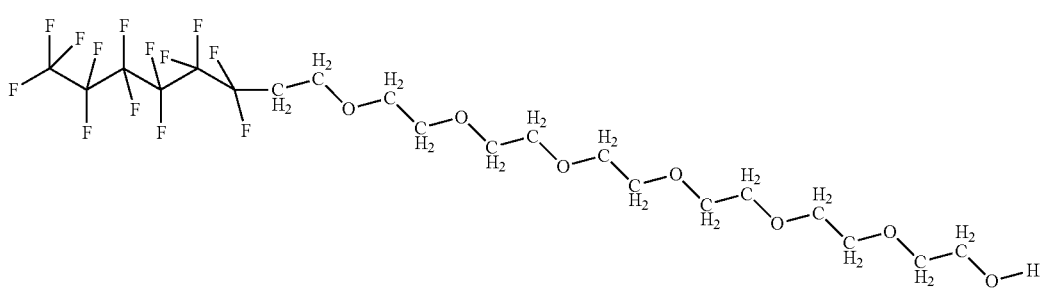

-continued
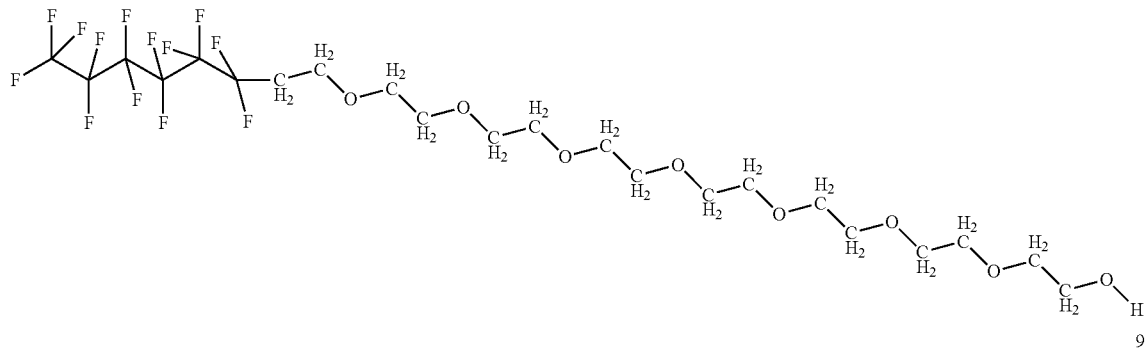
8
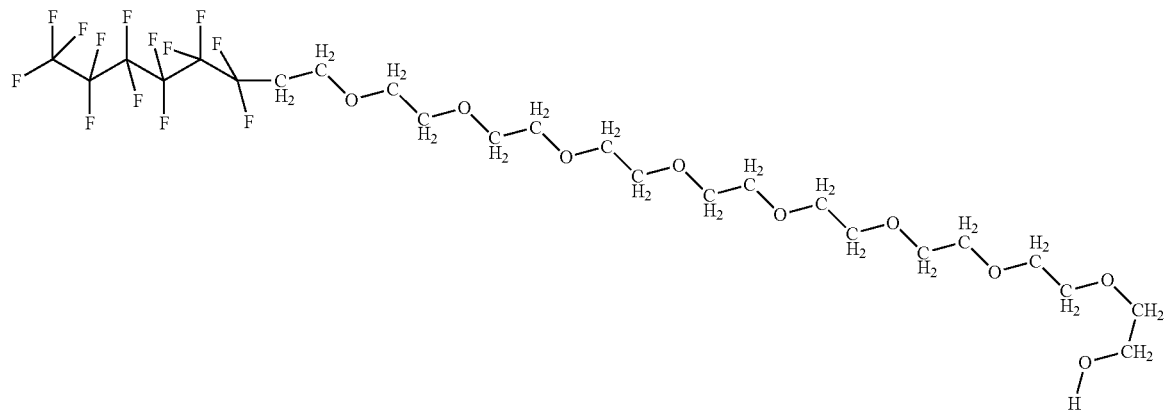
9
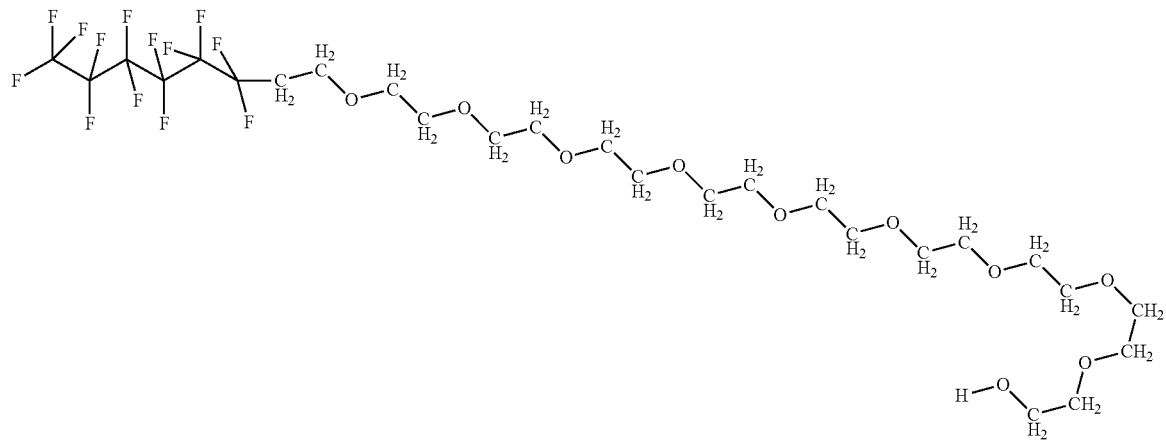
10
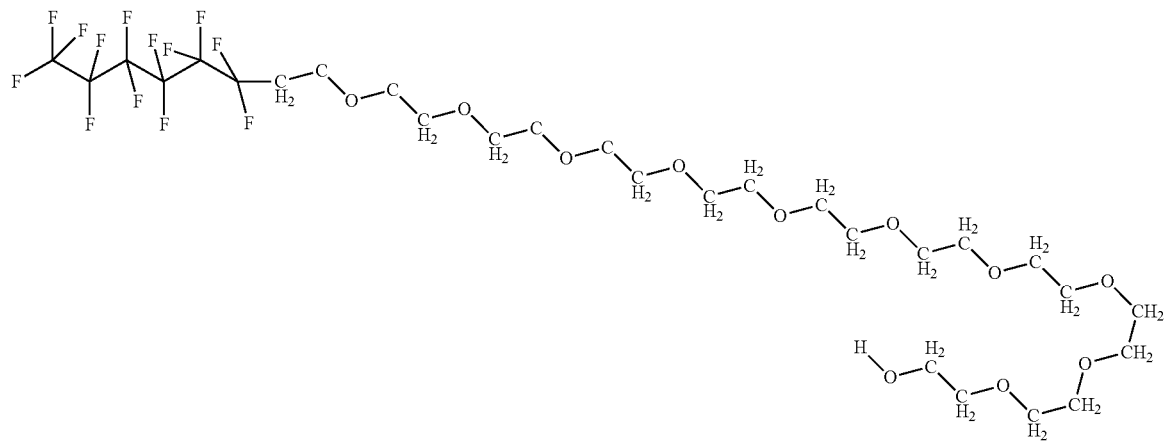
11

-continued
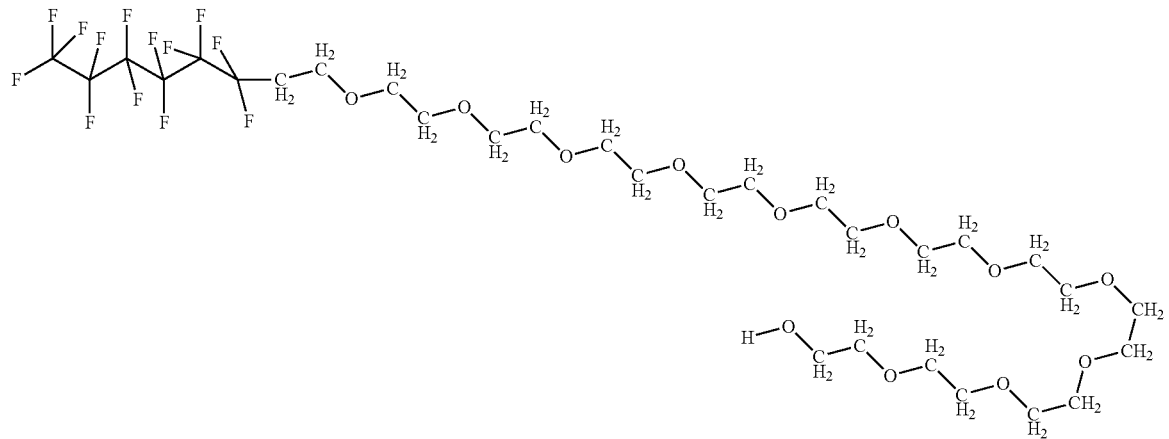
12
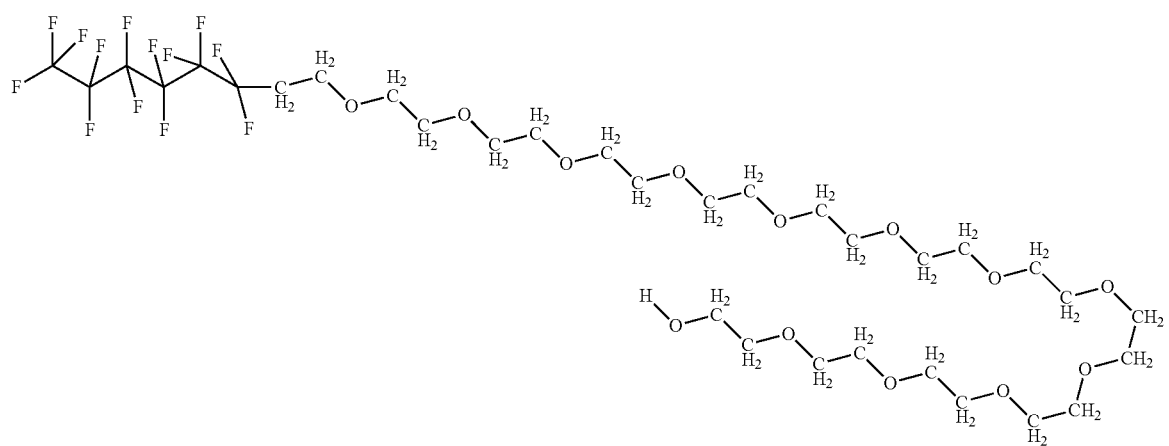
13
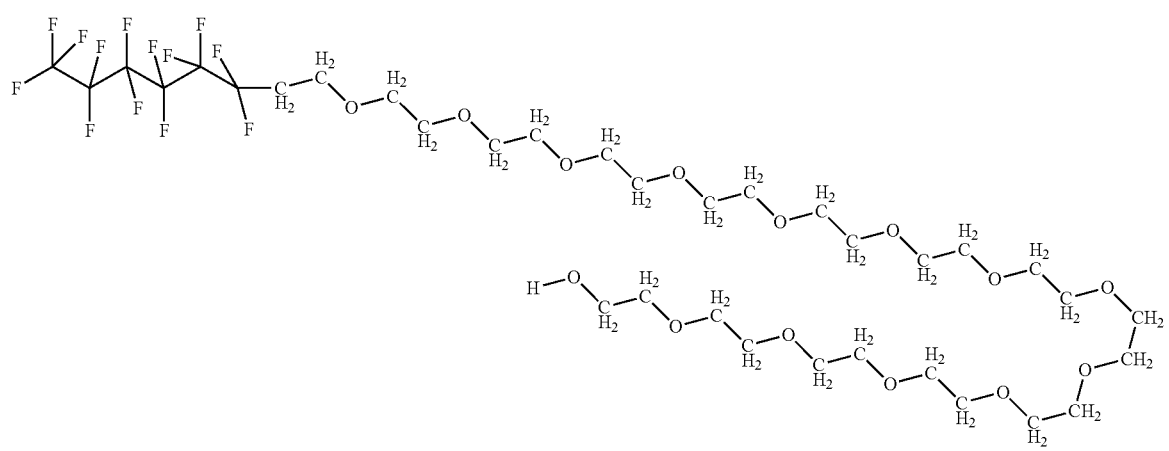
14

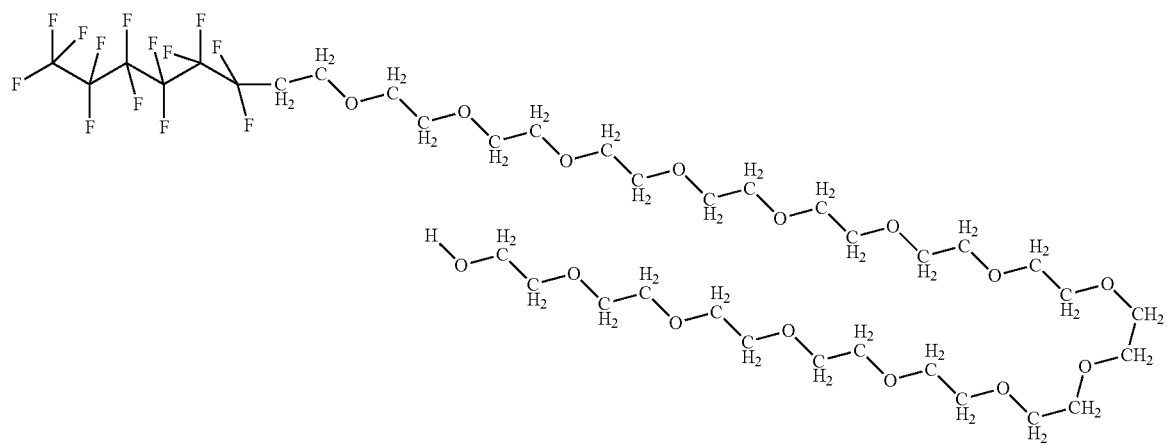

15

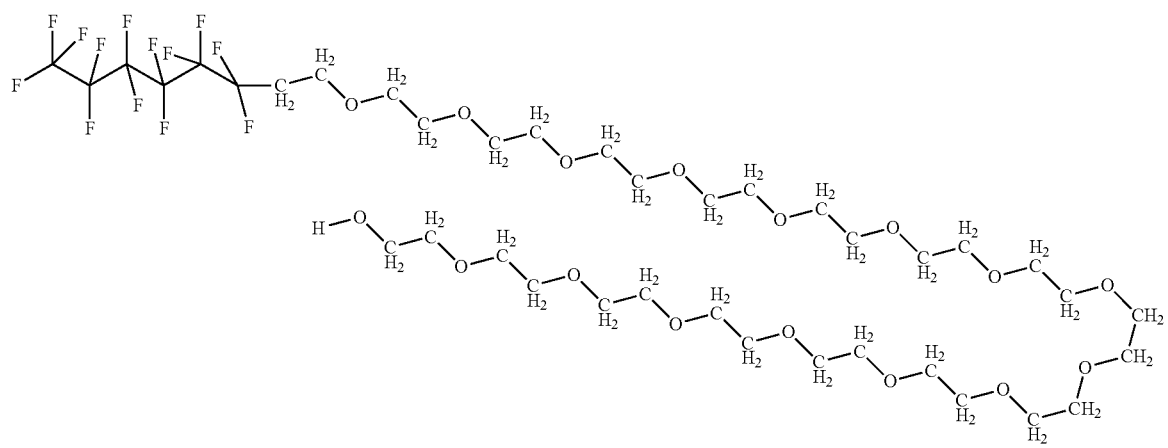

16

In certain embodiments, the fluorosurfactant consists of mixtures of compounds 1 to 16 which may contain any combination of those compounds and may omit any of those compounds singly or selected members of the set of compounds from 1 to 16.

In certain embodiments, other fluorocarbon surfactants comprising perfluoro-moiety 18 in combination with different foaming and wetting properties are used to form perfluorocarbon nanoemulsions of the invention. For example, other anionic surfactants based on sulfonic acids (DuPont FS-10) or phosphoric acid esters (DuPont FS-61, FS63, FS-64); zwitterionic and amphoteric surfactants (DuPont FS-50 and DuPont FS-51 respectively); nonionic surfactants, based on perfluoroalkylated polyethyleneoxy alcohols, such as DuPont FS-30, DuPont FS-31, DuPont FS-3100, DuPont FS34 and DuPont FS-35; and etc. can be utilized.

In certain embodiments, fluorocarbon-compound comprising moiety 18 in combination with differing length ethylene oxide moieties 19 are utilized to form perfluorocarbon nanoemulsions of the invention. In certain embodiments, n is between about 3 and about 6. In other embodiments, n is greater than or equal to 1 and less than or equal to about 16 to form stable nanoemulsions with low molecular weight perfluorocarbons, such as, dodecafluoropentane (DDFP), tetradecafluorohexane (TDFH), hexadecafluoroheptane (HDFH), and octadecafluorooctane (ODFO).

In some embodiments, pegylated perfluoroalkyloligoethyleneoxy alcohol surfactants of the form shown as compound 22

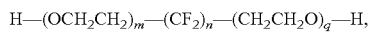 22 wherein independently m is an integer from 1 to about 50 (e.g., 1 to about 25, 1 to about 12, 1 to about 6, 6 to about 50, 12 to about 50, 25 to about 50), n is an integer from 1 to about 50 (e.g., 1 to about 25, 1 to about 12, 1 to about 6, 6 to about 50, 12 to about 50, 25 to about 50), and q is an integer from 1 to about 50 (e.g., 1 to about 25, 1 to about 12, 1 to about 6, 6 to about 50, 12 to about 50, 25 to about 50) are utilized to form perfluorocarbon nanoemulsions disclosed herein.

In certain more preferred embodiments a class of compounds that can be employed is selected from a subset of compound 22 shown below:

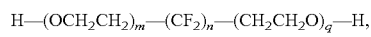

wherein m=1 to about 50, n=1 to 12 and q=1 to about 50.

In certain most preferred embodiments a class of compounds that can be employed is selected from a subset of compound 22 shown below:

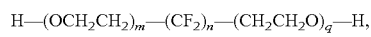

wherein m=from 1 to about 50, n=1 to about 6 and q=1 to about 50.

In certain embodiments individual members of the group of compounds or any combination of the individual members of the group of compounds represented as compound 22 are utilized as the fluorocarbon surfactant employed to form perfluorocarbon nanoemulsions disclosed herein.

In certain embodiments the mixture of compounds represented as structure 22 can be subjected to a custom refinement or purification protocol before being utilized to form perfluorocarbon nanoemulsions disclosed herein.

In certain embodiments any individual molecular species or combinations of individual members of the group of compounds represented by structure 22 can be subjected to a custom refinement or purification protocol before being utilized to form perfluorocarbon nanoemulsions disclosed herein.

In certain embodiments, an Ultra Turrax or similar dispersing apparatus can replace the magnetic stirring system to generate an initial coarse emulsion. The Ultra Turrax has a high-speed stirring motor (1,000-25,000 rpm), to which a dispersing element is attached to via a shaft. Therefore, it requires less time (0.5-5 min) to generate the coarse emulsion by using the Ultra Turrax compared by using the magnetic stirring system. Throughout the operation, the temperature of the solution is maintained at 2-6° C. to minimize any loss of low boiling perfluorocarbon liquid.

Further, vigorous agitation generated by using probe sonicators or homogenizers consisting of a high-speed motor and a dispersing attachment can be employed to make the coarse emulsion.

Subsequently, referring to Steps (140c)-(160c) or (140d)-(175d) of FIG. 1, the coarse emulsion is homogenized into a fine emulsion comprising mean particle diameters of less than or equal to 400 nm and a 99% cumulative distribution of which is less than or equal to 900 nm.

In one embodiment, a homogenizer (Avestin model C5) is used. In another embodiment, a homogenizer (Avestin model C50) is used. In another embodiment a Kirkland Products hand-held homogenizer with or without a pneumatic assist device is used. In certain embodiments, the homogenization pressure ranges from 1,000 psi to 14,000 psi. Further, in other embodiments, the homogenizer is used in continuous homogenization mode or in discrete homogenization mode. The number of discrete passes or the time for continuous homogenization can be adjusted to ensure achieving the fine emulsion.

Referring to FIG. 1, step (180), after the homogenization of the coarse emulsion to form a fine emulsion is completed, the resulting fine emulsion is transferred to another vessel containing a cooled (0-10° C.) stirred continuous phase consisting of WFI. Moreover, the continuous phase optionally contains a buffering agent, a viscogen, excipients, and preservatives (microbiocidal agents) to inhibit growth of any adventitiously introduced microbial species.

In certain embodiments, the transfer may be conducted by passing the emulsion from the first vessel through the homogenizer and into the second vessel with the homogenizer optionally pressurized. The volume of the dispersed phase is between 1 and 100-fold of the emulsion transferred. In certain embodiments, the fine emulsion is stirred for 10-30 minutes under nitrogen pressure (2-10 psi) to insure that the fine emulsion is homogeneously distributed throughout the continuous phase. A person having ordinary skill in the art will appreciate that the configuration of the apparatus and the scale of the preparation may require changes to the time employed in prior runs of different scale or using different equipment.

Figure 2:
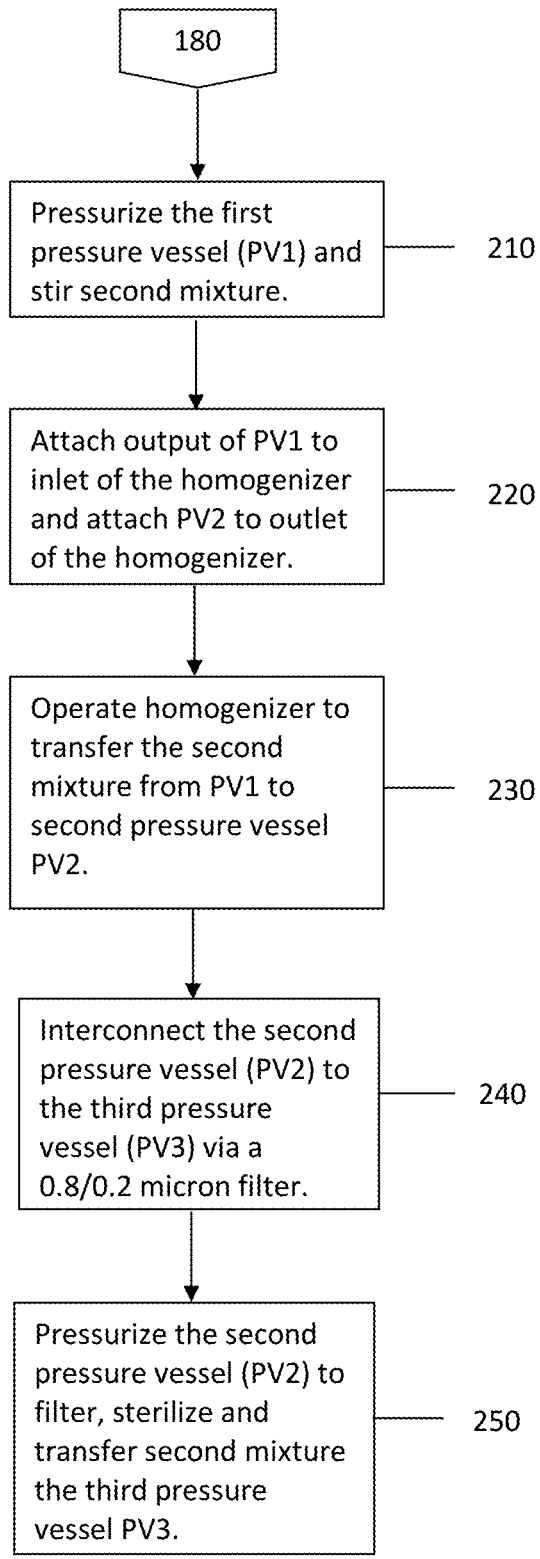
FIG. 2 is a flowchart summarizing additional steps in an exemplary embodiment of the method according to the invention of FIG. 1.
Figure 3:
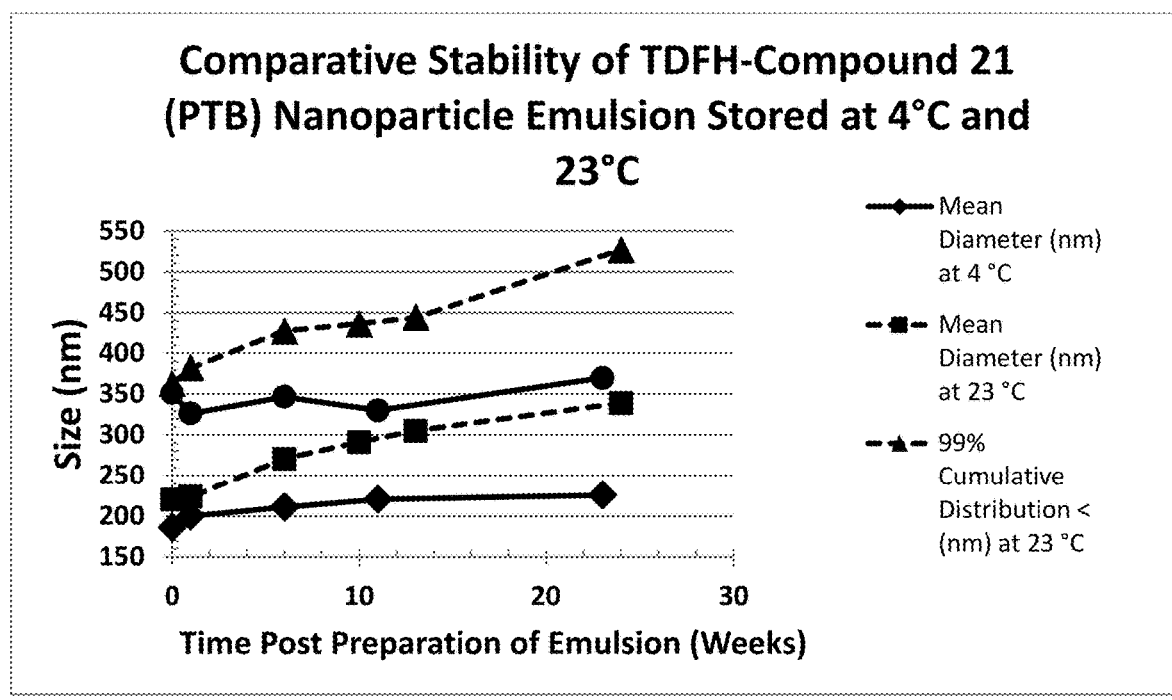
FIG. 3 graphically recites an exemplary embodiment of the method according to the invention stability data of TDFH-PTB nanoparticle emulsions stored at 4° C. and the same emulsions stored at 23° C.
Figure 4:
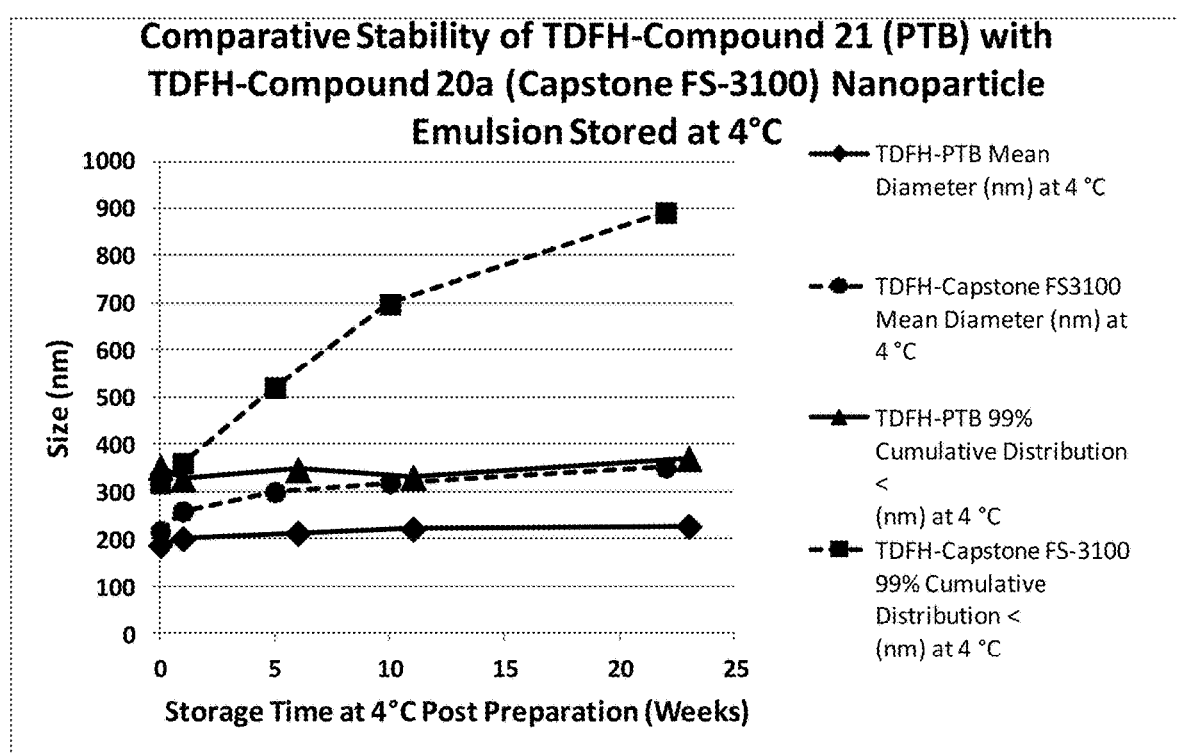
FIG. 4 graphically recites an exemplary embodiment of the method according to the invention stability data of TDFH-PTB nanoparticle emulsions stored at 4° C. and TDFH-Compound 20a (DuPont Capstone FS-3100) nanoparticle emulsions stored at 4° C.

In step (180), the method injects the fine emulsion into a sucrose solution disposed in a first pressure vessel (PV1) to form a second mixture. Referring to FIG. 2, in step (210), the method pressurizes the first pressure vessel (PV1) while stirring the second mixture of step (210).

In steps (220) and (230), the method transfers the second mixture into a second pressure vessel (PV2) using the homogenizer.

In steps (240) and (250) the method connects the second pressure vessel (PV2) to the third pressure vessel (PV3) via a 0.8/0/2 micron filter and then pressurizes the second pressure vessel to filter and sterilize the second mixture, and to transfer that second mixture to a third pressure vessel. In certain embodiments, the filtration step utilizes a syringe membrane filter, cartridge membrane filter, or a capsule membrane filter, or any other membranes that are made of materials compatible with the medium and are capable of removing particulate matter, including microbial entities, such as bacteria, mold, mold spores, and fungus contaminants, as small as 0.2 micron or even 0.1 micron. For example, the membrane material can be Supor® (polyethersulfone) membrane from Pall Sciences, the Pall EKV® filter series membrane, or Pall Sciences GHP Polypro® membrane.

After the step (250) is complete, the method stirs the resulting sterilized second mixture under a light pressure of nitrogen to insure homogeneous dispersion of the filtered solution. In certain embodiments, the method further transfers the filtered second mixture into capped and crimped vials using a peristaltic pump, a metering pump, a gear pump, or other suitable fluid transfer apparatus. Precautions to avoid microbial contamination during all of these operations are taken and such precautions for aseptic filling operations are known to the person having ordinary skill in the art.

Figure 6:
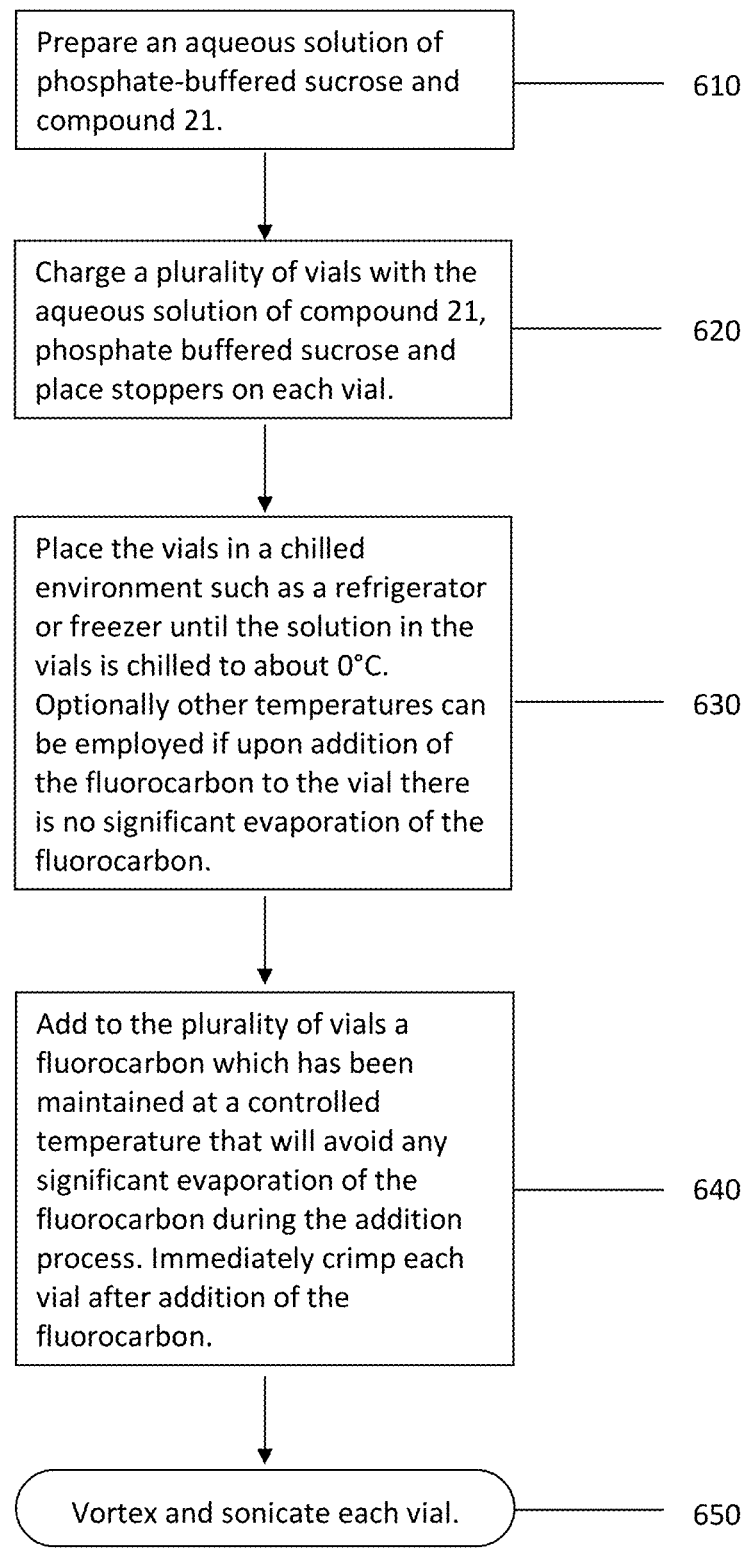
FIG. 6 is a flow chart summarizing an exemplary embodiment of the method according to the invention to form stabilized perfluorocarbon nanoemulsions comprising mixed components at their concentrations in the final product by vortexing and sonication.

Referring now to FIG. 6, in certain embodiments the nanoemulsions comprising a fluorocarbon surfactant 20a or 21 for example, can be prepared by sonication of the combined components. For example DDFP (as the neat liquid), phosphate-buffered aqueous sucrose (as a solution), and compound 20a surfactant (as the neat liquid or premixed with the aqueous phosphate buffered sucrose solution) are employed to prepare a nanoparticle emulsion of DDFP.

In step (610) the method prepares an aqueous solution of phosphate-buffered sucrose and fluorosurfactant compound 21 (Peg Telomer B). In step (620) the method charges a plurality of vials with the solution of step (610) and places stoppers over the mouth of each vial. In step (630) the method places the vials in a chilled environment that brings the vials to a temperature such that when the perfluorocarbon is added to the solution of the vial there is expected no significant amount of evaporation of the perfluorocarbon. In step (640) the fluorocarbon is added to each vial followed by immediate crimp capping of each vial. In step (650) the method subjects each vial to vortexing followed by sonication to generate perfluorocarbon nanoemulsions of the invention. In step (650) the components are initially mixed in the stoppered crimp capped vial by shaking or vortexing to create a coarse emulsion whose particle size distribution may range from about 200 nanometers to as high as 15 microns. The particle dimension sizes are illustrative and the person having ordinary skill in the art are aware that the dimensions in actual practice could fall below or above the given range.

Method of the invention then sonicates the vial, for example, in an ultrasonic cleaning bath such as a VWR Aquasonic 75HT unit, which provides a sonication frequency of about 40 KHz and a total power output of about 75-80 watts for a period of time between 1 second and 1 hour to form a desired particle-size distribution of the nanoparticle emulsion.

Figure 5:
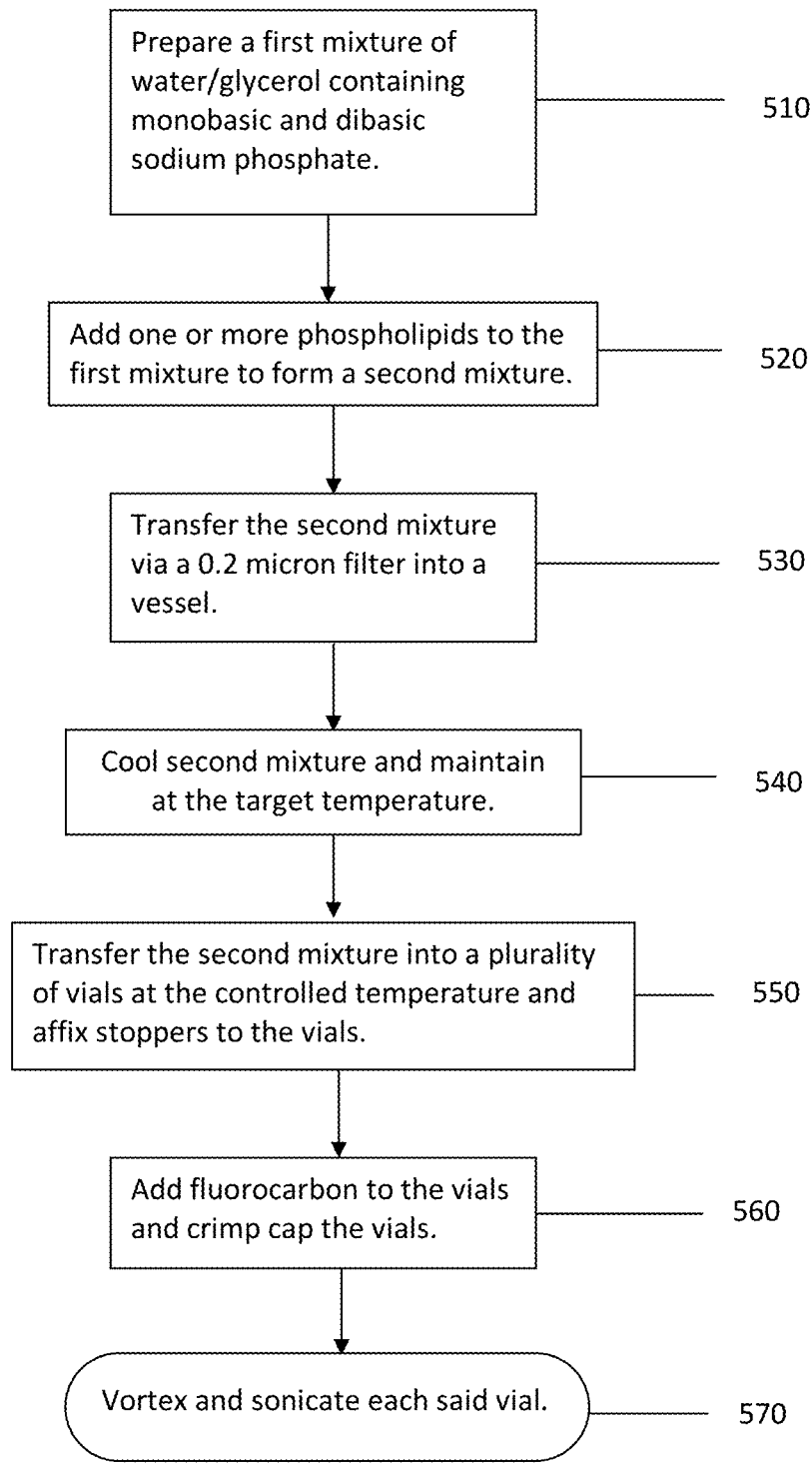
FIG. 5 is a flowchart summarizing an exemplary embodiment of the method according to the invention to generate phospholipids-stabilized-perfluorocarbon nanoemulsions.

Referring now to FIG. 5, in certain embodiments, one or more phospholipids are employed as an emulsifying surfactant system. Referring to FIG. 5 in step (510) the method prepares a first mixture of water and glycerol containing monobasic and dibasic phosphate buffer which is stirred at a temperature between ambient and 100° C. In step (520) phospholipids are added to the first mixture as solid material or as a solution in a suitable solvent at a temperature between ambient and 100° C. compatible with the process to form a second mixture. In step (530) the second mixture is filtered through a 0.2 micron filter into a second vessel. In step (540) the filtered solution is allowed to cool to ambient temperature if the temperature of its preparation exceeded ambient. In step (550) the method transfers the solution of step (540) into a plurality of vials and affixes stoppers to the vials. In step (560) the chosen fluorocarbon to be emulsified is added to the vials and the vials are immediately crimp capped. In step (570) the method vortexes and then sonicates said vials of step (560) for a time between 1 second and 1 hour in order to provide the fluorocarbon emulsion. The sonication time may be adjusted to provide particle size distributions of desired sizes which may be optimal for specific applications. In certain embodiments, the one or more phospholipids are saturated, partially saturated, or fully unsaturated. For example, a first nanoemulsion is formed using: DPPC (16:0), DPPE-MPEG-2000, or DPPE-MPEG5000, and optionally DPPE (16:0). A second nanoemulsion is formed using Egg yolk phospholipids singly or in combination with other added phospholipids or derivatized phospholipids. A third nanoemulsion is formed using 16:0-18:1 PC, 16:0-18:1 PE and 16:0-18:1 PE-MPEG2000, or 16:0-18:1 PE-MPEG5000. A fourth nanoemulsion is formed using DPPC (16:1), DPPE-MPEG-2000 or DPPE-MPEG-5000, and optionally DPPE (16:1). A fifth nanoemulsion is formed using DMPC, DMPE and DMPE-MPEG2000, or DMPE-MPEG5000. A sixth nanoemulsion is formed using 14:1 (Δ9-Cis) PC, 14:1 (Δ9-Cis) PE, 14:1 (Δ9-Cis) MPEG2000, or 14:1 (Δ9-Cis) MPEG5000. A sixth nanoemulsion is formed using; 14:1 (Δ9-trans) PC, 14:1 (49-trans) PE, 14:1 (Δ9-trans) MPEG2000, or 14:1 (Δ9-trans) MPEG5000. A seventh nanoemulsion is formed using DLPC (12:0), DLPE-MPEG-2000 or DLPE-MPEG-5000, DLPE (12:0).

Further, in certain embodiments, the relative proportions of the phospholipids components described herein can be varied to optimize the formulation with respect to solubility, emulsion stability, and oxygen uptake and release kinetics. For example, the first nanoemulsion can be formulated in a mole ratio of 82 DPPC (16:0), 8 DPPE (16:0)-MPEG-2000, and 10 DPPE (16:0) in a solution with water-propylene glycol-glycerol 85/10/5 v/v/v and a total lipids concentration of 0.75 mg/mL to as high as 50 mg/ml. Where lipid solubility is poor in the given diluents, the relative amounts of the propylene glycol and glycerol can be increased relative to water. The phospholipid components that can be employed are not limited to those described in the examples cited above. Certain formulations may require phospholipids mixtures consisting of a given fraction fully saturated phospholipids combined with a given fraction of their unsaturated congeners. The adjustments and tuning of properties, such as the gel to liquid crystal phase transition temperature, are well understood by the person having ordinary skill in the art.

In some embodiments, the addition of phospholipids with head groups that are homologous to those mentioned in the set of examples may be required. For example, when MPEG350 is employed instead of MPEG2000, the relative proportions of the components in systems that employ MPEG2000 can be different by needing a larger proportion of MPEG phospholipids compared to those with a choline head group. This also applies wherein PEGylated phospholipids or combinations of MPEG-phospholipids and PEG-phospholipids are employed as the surfactant system.

In some embodiments, choline type head groups may contain larger or smaller alkyl groups, or less than three alkyl groups.

In some embodiments, phospholipids with cationic moieties in their head groups such as diacyl phosphatidylethanolamine phospholipids, can be wholly or partially substituted with phospholipids bearing neutral head groups such as diacylphospatidyl glycerol phospholipids or anionic head groups such as diacyl phosphatidic acid.

In certain embodiments, small molecule substances can be employed as viscogen excipients, which can inhibit settling (inverse creaming) of the nanoparticulate fluorocarbon emulsion and adjust the overall density, viscosity, and tonicity of the solution to approximate that of blood into which the product solution is injected. For example, substances such as propylene glycol, glycerin, and sugar alcohols, such as sorbitol, xylitol, mannitol, and erythritol can be used as viscogens. Similarly, other polyhydroxy compounds such as mono-, di- or trisaccharides having appropriate solubility in the medium can serve as viscogens as well. Examples are fructose, glucose, xylose, sucrose, trehalose, raffinose, stachyose, alginates, cyclodextrins, substituted cyclodextrins, and dextrans. Furthermore, straight chain or multiarmed polyethylene glycols such as PEG300, PEG400, PEG600 and higher molecular weight PEGs up to MW 10,000, can also be employed as viscogens.

In certain embodiments, those skilled in the medical arts need to control the injection rate of the solution of the nanoemulsion to minimize the effects of tonicity mismatch between the solution of nanoemulsion and blood. However, the injected nanoemulsion needs not be isotonic. The said injected solution of nanoemulsion can be hypotonic or hypertonic so long as the degree of deviation from isotonicity does not result in discomfort to the patient or injury to tissue beyond transient effects.

In certain embodiments, the said nanoemulsion can be injected into a larger volume of a diluent such as 0.9% saline optionally containing other components such as a phosphate buffer as employed for preparation of phosphate buffered saline.

In certain embodiments, buffers other than sodium phosphate buffering systems may be employed to maintain the pH of the said nanoemulsions. Said buffers can be salts or combinations of the free acid form and salt form of, for example, acetic acid, arginine, aspartic acid, benzoic acid, carbonic acid, citric acid, gluconic acid, gluconic lactone, glycine, histidine, lysine, meglumine, phosphoric acid, or tromethamine; wherein acid salts are part of the buffering system. Further, the counterions are generally sodium, meglumine, or other cations that biochemically compatible and allowed for use in parenterals.

In certain embodiments, a chelating agent such as disodium EDTA can be used to sequester amounts of oxidizing metal ions such as $Fe^{3+}$ in order to protect nanoemulsions containing unsaturated phospholipids. Further, other antioxidant excipients, such as acetone sodium bisulfate, argon 100% in the headspace, ascorbyl palmitate, ascorbate (sodium/acid), bisulfite sodium, butylated hydroxyanisole (BHA), butylated hydroxytoluene (BHT), cysteine/cysteinate HCl, dithionite sodium (Nahydrosulfite, Nasulfoxylate), gentisic acid, gentisic acid ethanolamine, glutathione, formaldehyde sulfoxylate, sodium metabisulfite, potassium metabisulfite, methionine, nitrogen100% (in the headspace), propylgallate, sulfite sodium, tocopherol alpha, alpha tocopherol hydrogen succinate, or thioglycolate sodium, can be added to achieve the said protection.

Further, in certain embodiments, antimicrobials, such as benzalkonium chloride, benzyl alcohol, benzoic acid, chlorobutanol, m-cresol, myristyl gammapicolinium chloride, paraben methyl, paraben propyl, or Thimerosal in amounts that may range from 0.005% to 5% w/v depending on which of these is employed, can be added to the formulations.

Example 1

Experiments were conducted to study the particle size distribution of the nanoemulsions. Dodecafluoropentane [(DDFP) FluoroMed, Round Rock, Tex.] was emulsified at 2% (w/v) in a 30% (w/v) sucrose solution, buffered at physiological pH (~7). A purified medical grade form of fluorosurfactant, compound 21 (PEG-Telomer B), was used at a 0.3% (w/v) concentration in combination with an Emulsiflex C-5 homogenizer (Avestin, Ontario, Canada) to reduce and stabilize the particle size at ~250 nm. Because of the volatility of DDFP (BP 29° C.), stainless steel (316L) pressure vessels (PVs) with jackets for chilling were designed and fabricated for controlling the temperature and the pressurization of the product during the 3 phases of the compounding procedure. All process flow paths between PVs were staged with ¼ inch I.D. flexible nylon tubing. The ends of the tubing lines were fitted with mini-½ inch sanitary triclamp fittings that were chosen to smoothly and aseptically connect flow paths between the homogenizer and the PVs. Thus, the product was fully shielded from the room environment during the entire manufacturing process. The process temperature was controlled at 4-6° C. and the pressure in the vessel headspace was controlled at 5-7 psi using compressed nitrogen. The emulsion was recirculated (continuous homogenization) through the homogenizing valve for 6 passes (effectively) at 14,000 psi and then immediately filtered through a 0.2 μm sterile filtration capsule. Using a Unispence® (Wheaton, Millville, N.J.) filling machine, the resulting product was filled into 5 mL vials that were promptly stoppered by hand and crimped with a pneumatic Power Crimper (Kebby Industries).

The particle size distribution of the emulsion was assessed in triplicate at 0, 1, 2, 3 weeks and at 1, 2, 4, 6 and 11 months. At each time-point, 3 vials were selected at random and analyzed by dynamic light scattering using a PSS Nicomp 380 DLS submicron particle sizer (Particle Sizing Systems, Port Richie, Fla.). In order to minimize the effect of gradual temperature increase during size determinations, the sample temperature was controlled at 19° C.

The average particle size, which is given as the intensity weighted mean diameter (IWMD), did not exceed 260 nm. Furthermore, 99% of the particles were measured to have diameter less than or equal to 400 nm throughout the study. Less than 0.8% of the total volume of particles consisted of particles between 0.5μ and 50μ.

Example 2

Experiments were conducted to study the size of submicron particles, the size of particles in the region 0.5 to 50 microns, the stability of nanoparticle emulsions at different temperatures, using TDFH/Compound 21 (PTB).

A 6% solution of custom purified medical grade compound 21 (J. Tech Sales, Boca Raton, Fla.) was prepared by combining a 1.2 g aliquot of the compound 21, wherein y is 5 and wherein n is 1 through 16, diluting to the mark of a premeasured 20 mL volume in a glass scintillation vial with water for injection (HyPure® from Hyclone), and stirring at 5° C. for 0.5 hr using a small cross-shaped magnetic stirrer. The solution was stored in the refrigerator at 4° C. The previously prepared solution of compound 21 in water was removed from the refrigerator and a 12.12 mL portion was added to a 15 mL RB flask (total capacity 21 mL) equipped with a small barrel-shaped magnetic stir bar. Then cold (4° C.) TDFH (Sigma Aldrich Co. St. Louis, Mo.), 3.17 mL, (5.29 g) was added and the flask was capped with a 14/20 rubber septum and was immersed into a 2° C. ice-water bath. The mixture was stirred for 1 h.

During the stirring period the syringe cooling tank and the PV1-PV3 cooling tank were charged with ice-water. The pressure vessels containing floating magnetic stirrers were fitted with their caps, each of which bears a Swagelok™ bottom-entry two-position instrument ball valve attached to a 0.25" OD 316SS dip tube (for introduction and withdrawal of product from the vessels) and a three-way three-position stop cock which serves as a nitrogen inlet and a venting system. The PV1 with cap and large cross-shaped stirrer was charged with the solution of phosphate-buffered sucrose (216.8 mL) and placed into the PV1-PV3 cooling tank and stirring was initiated. PV2 was placed in the tank and by appropriate placement in the proximity of PV1 so that both stirrers were in motion. PV3 was placed in an ice bath for cooling prior to receipt of product from PV2. A 0.8/0.2 micron Pall Acrodisc™ (Supor membrane) was readied for attachment to the instrument valve inlet of PV3.

A Kirkland products hand-held homogenizer ("homogenizer") was purged of resident WFI and then rinsed with cold WFI (25 mL). Cold-jacketed 25 mL glass Perfektum MicroMate™ syringes with glass plungers were attached to the input and output Luer lock fittings of the homogenizer. The receiving syringe was fitted with a two-way stopcock with Luer fittings. The input gas line (80 psi) was connected to the pneumatic piston unit of the homogenizer. At completion of the stirring period for the primary emulsion, the output syringe was removed from the homogenizer and fitted with a 17-gauge needle. The primary emulsion was withdrawn into the syringe, then the needle was removed and the syringe was rapidly affixed to the input side of the homogenizer. A BioRad Econopump peristaltic pump was employed to pump ice water through the syringes in series from the syringe bath cooling tank. The peristaltic pump was fitted with two lengths of ⅛" diameter Pharmed® tubing which were joined at the input and output sides using Y connectors in order to access a total flow rate of 38 mL/min. The coolant lines from the peristaltic pump were attached in series to the output syringe and the input syringe and the circulation of the coolant was initiated. The bypass valve of the homogenizer was opened and the primary emulsion was transferred several times between the output syringe and the input syringe by alternate depression of the syringe plungers; the final position of the primary emulsion was in the input syringe. The bypass valve was closed and the pneumatic unit operation was initiated at a pumping rate of ~30 mL/min. When the contents of the input syringe were fully transferred to the output syringe the bypass valve was rapidly opened, the plunger of the output syringe was depressed to quickly transfer the homogenized primary emulsion back to the input syringe, the bypass valve was closed and the second pass was begun. In this manner the primary emulsion was subjected to 20 discrete passes through the homogenizer. At the end of this procedure the primary emulsion was the output syringe.

The output syringe was disconnected from the homogenizer outlet and the needle put about 2 inches below the surface of the stirred solution in PV1. The primary emulsion was injected from the syringe into PV1. PV1 was pressurized with nitrogen (~8-10 psi) and the mixture was stirred for about 5 minutes during which time 1/16" tubing (braided silicone-platinum cured) was connected from the dip tube stopcock of PV1 to the input side of the homogenizer and from the PV2 dip tube stopcock to the output side of the homogenizer. The nitrogen pressure was maintained in PV1 and PV2 was vented to atmosphere. The dip tube ball valve of PV2 was opened followed by that of PV1 with simultaneous starting of the homogenizer. This resulted in transfer of the stirred solution of the primary emulsion in the 32% sucrose solution from PV1 to PV2 in a single pass through the homogenizer. After transfer of the solution to PV2, PV1 was removed from the PV1-PV3 cooling tank and the PV2-PV3 pair were positioned so that stirring was obtained in both. The Pall Sciences Acrodisc 20™ 0.8/0.2 micron filter was attached between PV2 and PV3 via the dip tube ball valve inlet/outlet. Then PV2 was pressurized with nitrogen initially at ~12 psi to initiate transfer filtration of the solution in PV2 to PV3. The filtration required about 30-40 min to complete and the transfer was nearly quantitative.

The filtered solution in PV3 was transferred to a crystallization dish containing ice water, stabilized with a clamp, pressurized to about 8 psi with nitrogen and the solution within was stirred for ~15 min. After this time two Wheaton vial trays with 50 nominal 2 mL serum vials (total capacity 3 mL) with gray butyl rubber stoppers were removed from the refrigerator. A 1/16" i.d. braided silicone tube fitted with a 12 gauge SS tube on its output side was connected to the output of the instrument valve on PV3. The pressure in PV3 was adjusted to about 5 psi and the dip tube stopcock was opened to the tubing. The vials were filled (in groups of 10) by removing the notched stopper from the vial, opening and closing the stopcock at the distal end of the tubing attached to PV3, and replacement of the notched stopper.

After 10 vials were filled they were stoppered and crimp capped. This was repeated until the solution in PV3 was consumed. This gave 65 vials with a fill volume of 2.6-2.7 mL. The vials in the tray were stored at 4° C. for stability studies. A second tranche of material was prepared in the same manner and was stored at 23° C. to probe the effect of storage temperature on particle stability.

TABLE 1

Submicron Particle Sizing of TDFH-compound 21 Nanoemulsion Stored at 4° C. by Dynamic Light Scattering Using the Nicomp 380 DLS

| Vial No. | IWMD (nm) | Standard Deviation (nm) | 99% Cumulative Distribution (nm) |
|---|---|---|---|
| 1 | 186.9 | 56.1 | <358.9 |
| 10 | 184.5 | 67.7 | <404.8 |
| 18 | 187.8 | 45.8 | <321.3 |
| 26 | 189.2 | 45.4 | <321.1 |
| 34 | 183.7 | 54.7 | <351.2 |
| Average | 186.4 | 53.9 (28.9%) | <351.5 |
| Std Dev | 2.29 | 9.13 | 34.39 |
| RSD (%) | 1.23 | 16.93 | 9.79 |

Submicron particle sizing data using a PSS Nicomp 380 DLS Submicron Particle Sizer (Particle Sizing Systems, Port Richie, Fla.) obtained immediately post preparation is displayed in Table 1. The average particle size of the TDFH-compound 21 nanoemulsion measured in IWMD does not vary and remains well within the specification for release. Furthermore, 99% of the particles were measured to have diameter less than or equal to 400 nm throughout the study.

TABLE 2

Particle Sizing of TDFH-compound 21 Nanoemulsion Stored at 4° C. by Single Particle Optical Sensing Using the PSS Accusizer 780 SIS 0.5-500 microns

| Vial No. | Total # Particles Sized > Threshold of 0.5 micron | # of Particles Sized 5.02-50.45 microns | Volume % of entire emulsion occupied by particles sized 5.02-50.45 microns |
|---|---|---|---|
| 2 | 62145 | 690 | 0.899 |
| 16 | 58232 | 779 | 0.746 |
| 31 | 55441 | 544 | 0.714 |
| Average | 58606 | 671 | 0.786 |
| Std. Dev. | 3368 | 118.65 | 0.10 |
| % RSD | 5.75 | 17.68 | 12.57 |

Particle size data in the region 0.5 to 50 microns was obtained using a PSS 780 SIS light obscuration instrument (Particle Sizing Systems, Port Richie, Fla.) and is displayed in Table 2. Less than 0.8% of the total volume of particles consisted of particles between 0.5μ and 50μ and major volume of particles consisted of particles smaller than threshold of 0.5 micron.

Data for particle size and 99% cumulative distribution at 4° C. and 23° C. is provided in Table 3 and Table 4, respectively.

TABLE 3

Particle Stability with Time for TDFH-compound 21 Nanoemulsion Stored at 4° C.

| Time Post Preparation (Weeks) | IWMD (nm) | Std Dev (nm) | SD % | 99% Cumulative Distribution < (nm) |
|---|---|---|---|---|
| 0 | 186.4 | 53.9 | 28.9 | 351.5 |
| 1 | 200.1 | 43.3 | 21.6 | 326.4 |
| 6 | 211.3 | 47.1 | 22.3 | 346.7 |
| 11 | 220.9 | 39.6 | 17.9 | 330.3 |
| 23 | 225.9 | 49.5 | 21.9 | 370.0 |

When TDFH-compound 21 nanoemulsion was stored at 4° C., the average particle size of the particles measured in IWMD changes very slowly and remains well within the specification for release. Furthermore, 99% of the particles were measured to have diameter≤400 nm throughout the study.

TABLE 4

Particle Size Stability Data for TDFH-compound 21 Nanoemulsion Stored at 23° C.

| Time Post Preparation (Weeks) | IWMD (nm) | Standard Deviation (nm) | 99% Cumulative Distribution (nm) |
|---|---|---|---|
| 0 | 220.2 | 49.7 | <363 |
| 1 | 223.7 | 54.3 | <382.2 |
| 4 | 257.4 | 42.7 | <374.5 |
| 6 | 270.7 | 55.6 | <427.3 |
| 8 | 282.4 | 48.9 | <417.6 |
| 10 | 291.1 | 52.6 | <436.1 |
| 13 | 305.3 | 51.0 | <443.9 |

TABLE 4-continued

Particle Size Stability Data for TDFH-compound 21 Nanoemulsion Stored at 23° C.

| Time Post Preparation (Weeks) | IWMD (nm) | Standard Deviation (nm) | 99% Cumulative Distribution (nm) |
|---|---|---|---|
| 19 | 322.1 | 65.6 | <506.7 |
| 24 | 339.2 | 67.0 | <526.8 |

When TDFH-compound 21 nanoemulsion was stored at 23° C., the average particle size of the particles measured in IWMD changes slowly but still remains well within the specification for release. Furthermore, 99% of the particles were measured to have diameter≤530 nm throughout the study.

TABLE 5

Change in Particle Size and 99% Cumulative Distribution < with Time for TDFH-compound 21 Stored at 4° C. and 23° C.

| Time Post Prep (Weeks) | IWMD (nm) at 4° C. | IWMD (nm) at 23° C. | 99% Cumulative Distribution < (nm) at 23° C. | 99% Cumulative Distribution < (nm) at 4° C. |
|---|---|---|---|---|
| 0 | 186.4 | 220.0 | 363.0 | 351.5 |
| 1 | 200.1 | 223.7 | 382.2 | 326.4 |
| 6 | 211.3 | 270.7 | 427.3 | 346.7 |
| 10 |  | 291.1 | 436.1 |  |
| 11 | 220.9 |  |  | 330.3 |
| 13 |  | 305.3 | 443.9 |  |
| 23 | 225.9 |  |  | 370.0 |
| 24 |  | 339.2 | 526.8 |  |

The above data showed in Table 3, Table 4, and Table 5 clearly demonstrates that the TDFH-compound 21 nanoemulsion remains well within the specification for release and for shelf life at storage temperature of 4° C. and 23° C. Further, the trend in the data indicates that the shelf life specification would not be exceeded at 26 weeks.

Example 3

Nanoparticle Emulsion of Tetradecafluoro-n-hexane (TDFH) and Compound 20a Prepared by High-Pressure Homogenization.

Experiments were conducted to analyze the particle size of the nanoparticle emulsion of TDFH and compound 20a, the particle size of nanoparticle emulsion of TDFH and compound 20a at 4° C., the stability of the particle size of the nanoparticle emulsion of TDFH and compound 20a at 23° C., and the change in particle size and 99% cumulative distribution with time for TDFH-compound 20a and TDFH-compound 20a stored at 4° C.

A 6% solution of compound 20a (J. Tech Sales, Boca Raton, Fla.) (20 mL) was prepared by adding a 1.2 g aliquot of the surfactant, diluting to the mark of a premeasured 20 mL volume in a glass scintillation vial with water for injection (HyPure from Hyclone), and stirring at 5° C. for 0.5 hr using a small cross-shaped magnetic stirrer. The solution was clear at 5° C. and was stored in the refrigerator (3° C.). This solution can be stored and employed for different experiments.

A 6.25 mL portion of the solution of compound 20a was added to a 15 mL serum vial equipped with a small barrel-shaped magnetic stir bar. Then cold (4° C.) TDFH (Sigma Aldrich Co. St. Louis, Mo.) 1.52 mL (2.53 g) was added and the vial was capped with a rubber septum, immersed into an ice-water bath (2° C.), and the mixture was stirred 1 h at that temperature.

A rectangular stainless steel pan containing a cooling bath tank for circulation through syringe cold jackets and a separate cooling bath for the pressure vessels was removed from the refrigerator and both charged with ice-water. PV1, PV2, and PV3, which each is a 125 mL vessel fitted with accessories as for the larger vessels containing large cross-shaped magnetic stirrers described in Example 2, were fitted with their caps with appropriate valved inlets and outlets for product and nitrogen gas. PV1 was charged with 10 mM phosphate-buffered (pH 7) sucrose (32% wt/vol sucrose, 104 mL) and placed into the PV1-PV3 cooling tank and stirring was initiated. PV2 and PV3 were placed in the tank as well and stirring was initiated.

A homogenizer fitted to a pneumatic pumping unit was purged of resident WFI and then rinsed with cold WFI (25 mL). Cold-jacketed 10 mL glass Popper and Sons syringes with glass plungers were attached to the input and output Luer lock fittings of the homogenizer. The bypass valve of the homogenizer was opened and the primary emulsion was transferred several times between the output syringe and the input syringe by alternate depression of the syringe plungers, wherein the final position of the primary emulsion was in the input syringe. The bypass valve was closed and the pneumatic unit operation was initiated at an approximate pumping rate of 30 mL/min. When the contents of the input syringe were fully transferred to the output syringe, the bypass valve was rapidly opened, then the plunger of the output syringe was depressed to quickly transfer the homogenized primary emulsion back to the input syringe, then the bypass valve was closed, and the second pass was begun. In this manner the primary emulsion was subjected to 20 discrete passes through the homogenizer. The primary emulsion was in the output syringe at the end of this operation.

The output syringe was disconnected from the homogenizer outlet, attached to PV1 and the primary emulsion was injected from the syringe into PV1. PV1 was pressurized with nitrogen (~8-10 psi) and the mixture was stirred for about 5 minutes. The nitrogen pressure was maintained in PV1 and PV2 was vented to atmosphere. The transfer of the stirred solution of the primary emulsion mixed with the 32% sucrose solution in PV1 to PV2 was accomplished in a single pass through the homogenizer. Then a Pall Sciences 32 mm 0.8/0.2 micron Acrodisc syringe filter was attached between PV2 and PV3. PV2 was pressurized with nitrogen at ~12 psi and PV3 was vented to the atmosphere to initiate filtration/transfer of the solution from PV2 to PV3. After ~5 min the pressure was increased to 15 psi and after about 10 min up to 25 psi. The filtration required about 30-40 min to complete and the transfer was nearly quantitative.

PV3, cooled at ~4° C., was pressurized to about 8 psi with nitrogen and the solution within was stirred for ~15 min. After this time a Wheaton vial tray charged with 402 mL (nominal volume) serum vials fitted with gray butyl rubber notched stoppers was removed from the refrigerator. A 1/16" i.d. braided silicone tube fitted on its input side with a male luer lock connector and on its output side with a female luer fitting connected to a double male luer connector, a one way stopcock (in closed position) and finally a 16 gauge needle, was affixed to the dip tube stopcock of PV3. The pressure in PV3 was adjusted to 5 psi and the first 2 mL of the solution was rejected. Then the vials were filled (in groups of 10) by removing the notched stopper from the vial, opening and closing the stopcock at the distal end of the tubing attached to PV3, and replacing of the notched stopper. After 10 vials were filled, they were hand crimped. This procedure was repeated until the solution in PV3 was consumed, which resulted in 34 vials with an approximate fill of 2.6-2.7 mL (~88-91% product yield). The vials were inspected for crimp tightness and, where needed, re-crimped to assure a tight crimp. The vials were stored in the refrigerator at 4° C. for stability studies.

The average particle size of the TDFH-compound 20a nanoemulsion, measured in IWMD, is about 216 nm and does not vary much among different samples. Further, the average 99% cumulative distribution of the TDFH-compound 20a nanoemulsion is less than 318 nm.

TABLE 6

Submicron Particle Sizing of TDFH-compound 20a Nanoemulsion Stored at 4° C. by Dynamic Light Scattering Using the PSS Nicomp 380 DLS

| Vial No. | IWMD (nm) | Standard Deviation (nm) | 99% Cumulative Distribution (nm) |
| --- | --- | --- | --- |
| 1 | 217.0 | 17.8 | <261.6 |
| 10 | 213.2 | 28.8 | <289.1 |
| 18 | 220.0 | 22.7 | <278.0 |
| 26 | 213.5 | 56.6 | <381.6 |
| 34 | 216.3 | 55.6 | <380.4 |
| Average | 216.0 | 36.3 (16.8%) | <318.1 |
| Std Dev | 2.79 | 18.5 | 58.2 |
| RSD (%) | 1.29 | 51.0 | 18.3 |

Particle size analysis of the product immediately post preparation was carried out using a Nicomp 380 DLS submicron particle sizer (Particle Sizing Systems, Port Richie, Fla.) on 5 vials of material selected from across the entire range of filled vials.

TABLE 7

Particle Sizing of TDFH-Compound 20a Nanoemulsion Stored at 4° C. by Single Particle Optical Sensing Using the PSS Accusizer 780 SIS 0.5-500 microns

| Vial No. | Total # Particles Sized > Threshold of 0.5 micron | # of Particles Sized 5.0-50. microns | Volume % of entire emulsion occupied by particles sized 5.02-50.45 microns |
| --- | --- | --- | --- |
| 2 | 134919 | 422 | 1.12 |
| 16 | 182911 | 405 | 0.53 |
| 33 | 180519 | 296 | 1.12 |
| Average | 166116 | 374 | 0.923 |
| Std. Dev. | 27044 | 68.37 | 0.340 |
| % RSD | 16.28 | 18.26 | 36.69 |

Particle sizing in the 0.5 to 50 micron regime was performed by light obscuration using the PSS Accusizer 780 SIS (Particle Sizing Systems, Port Richie, Fla.). On average, around 0.9% of the total volume of the entire TDFH-compound 20 nanoemulsion contains particles sized between 5.02-50.45 microns.

TABLE 8

Particle Size Stability Data for Compound TDFH-Compound 20a Nanoemulsion Stored at 4° C.*

| Time Post Prep. Weeks | IWMD (nm) | | | Standard Deviation (nm) | | | 99% Cumulative Distribution < (nm) | | |
| --- | --- | --- | --- | --- | --- | --- | --- | --- | --- |
| | Mean (nm) | Mean Std. Dev. | RSD | Mean (nm) | Mean Std. Dev. | RSD | Mean (nm) | Mean Std. Dev. | RSD |
| 0 | 216.0 | 2.79 | 1.29 | 36.3 | 18.49 | 50.95 | 318.1 | 58.21 | 18.3 |
| 1 | 257.9 | 2.34 | 0.91 | 37.7 | 13.68 | 36.27 | 360.0 | 41.81 | 11.6 |
| 5 | 299.0 | 7.98 | 2.67 | 74.3 | 23.26 | 31.32 | 520.1 | 82.63 | 15.9 |
| 10 | 318.0 | 4.65 | 1.46 | 116.7 | 7.92 | 6.78 | 698.0 | 36.88 | 5.28 |
| 22 | 351.0 | 7.45 | 2.12 | 155.7 | 10.32 | 6.63 | 892.0 | 48.52 | 5.44 |

*N = 3 for each time point

TABLE 9

Change in Particle Size and 99% Cumulative Distribution < with Time for TDFH-Compound 21 and TDFH-Compound 20a Stored at 4° C.*

| Time Post Prep. (Weeks) | TDFH-Compound 21 IWMD (nm) at 4° C. | TDFH-Compound 20a IWMD (nm) at 4° C. | TDFH-Compound 21 99% Cumulative Distribution < (nm) at 4° C. | TDFH-Compound 20a 99% Cumulative Distribution < (nm) at 4° C. |
| --- | --- | --- | --- | --- |
| 0 | 186.4 | 216 | 351.5 | 318.1 |
| 1 | 200.1 | 257.9 | 326.4 | 360.0 |
| 5 | | 299.0 | | 520.1 |
| 6 | 211.3 | | 346.7 | |
| 10 | | 318.0 | | 698.0 |
| 11 | 220.9 | | 330.3 | |
| 22 | | 351.0 | | 892.0 |
| 23 | 225.9 | | 370.0 | |

*N = 3 for each time point

Example 4

Nanoparticle Emulsion of DDFP and Compound 20a Prepared by High-Pressure Homogenization Experiments were conducted to study the submicron particle size of DDFP-Compound 20a nanoemulsions prepared by high-pressure homogenization. The nanoemulsion was prepared by the method of Example 3 except that DDFP (Fluoromed, Round Rock, Tex.) was substituted in place of TDFH. Submicron particle sizing was performed using a PSS Nicomp 380 DLS submicron particle sizing instrument (Particle Sizing Systems, Port Richie, Fla.).

TABLE 10

Submicron Particle Sizing of DDFP-DuPont Compound 20a Nanoemulsion Prepared by High Pressure Homogenization: Using the Nicomp 380 DLS Submicron Particle Sizer

| Vial No. | IWMD (nm) | Standard Deviation nm, % | 99% Cumulative Distribution (nm) |
|---|---|---|---|
| 19 | 238 | 68.8, 28.9% | 446.8 |
| 7 | 234.8 | 52.4, 22.3% | 384.6 |
| Average | 236.4 | 60.6, 25.6% | 415.7 |

The intensity weighted mean diameter of 236.4 nm and 99% cumulative distribution less than 415.7 nm of the submicron particle size of DDFP-Compound 20 nanoemulsions are essentially equivalent to the initial values obtained for nanoemulsion of DDFP-compound 21, TDFH-compound 21 and TDFH-compound 20a.

Example 5

Nanoparticle Emulsion of DDFP and Compound 20a Prepared by Vortexing Followed by Sonication Experiments were conducted to study the submicron particle size of DDFP-Compound 20a nanoemulsions prepared by vortexing followed by sonication. A 262 mL total capacity cylindrical glass bottle was equipped with a floating magnetic stir bar and a threaded lid equipped with two gas inlets and a two-position bottom entry ball valve-dip tube combination and was purged with dry ultrapure nitrogen gas. Then aqueous (WFI, Hypure from Hyclone) phosphate buffered (10 mM $NaH_2PO_4/Na_2HPO_4$, pH 6.9) sucrose (30% w/v) 210 mL and compound 20 (J. Tech Sales, Boca Raton, Fla.) solution (0.672 gin 10.68 mL of 0.2 micron filtered distilled deionized water) were combined in the 262 mL vessel and stirred with cooling at 4° C. After 5 minutes of stirring the vessel was pressurized to 3 psi with nitrogen. One of the outlets of the ball valve was fitted with Dow Corning Silastic® tubing (⅛" o.d.) which was connected to a 3 way sterile single use stopcock via a Luer to ⅛" barb adaptor. The remaining two ports were fitted with a 10 mL Becton and Dickinson (Franklin Lakes, N.J.) sterile disposable syringe and 18-gauge 1.5" sterile disposable needle.

The three-way stopcock was positioned to allow aspiration of solution from the vessel into the syringe until a volume of 7.8 mL was loaded into the syringe. Then the position of the stopcock was set to allow delivery of solution from the syringe through the 18 gauge needle. A tray of 25 nominal 5 mL capacity (9 mL total capacity) serum vials (purged with dry nitrogen gas, fitted with halobutyl stoppers, and kept in a 4° C. refrigerator for 1 h) was charged with 7.8 mL aliquots of the solution by lifting the stopper slightly, positioning the needle tip in the mouth of the vial, and depressing the syringe plunger followed by rapid replacement of the stopper. After all of the vials were charged with the solution, each vial was quickly charged with cold (~0° C.) DDFP (0.156 g, 0.089 mL) using a Becton and Dickinson 0.5 mL Lo Dose U-100 insulin syringe and immediately stoppered and crimp was capped.

For preparation of nanoparticles, a vial was vortexed at 4500 rpm for 1 min upright, 1 min inverted, and 1 min upright. Then the vial was positioned up to the neck in the center of a VWR Aquasonic 75HT ultrasonic cleaning bath and sonicated for 5 minutes. A second vial was processed in the same manner and the particle size and distribution were analyzed using the PSS Nicomp 380 DLS submicron particle sizer (Particle Sizing Systems, Port Richie, Fla.).

TABLE 11

Submicron Particle Sizing of DDFP-Compound 20a Nanoparticle Nanoemulsion Prepared by Vortexing and Sonication Using the Nicomp 380 DLS Submicron Particle Sizer

| Vial No. | IWMD (nm) | Standard Deviation nm, % | 99% Cumulative Distribution (nm) |
|---|---|---|---|
| 2 | 274 | 95.1, 34.7% | 578 |
| 22 | 275 | 105.3, 38.3% | 622 |
| Average | 274.5 | 100.2, 36.5% | 600 |

The mean diameter of 274.5 nm and 99% cumulative distribution less than 600 nm of the submicron particle size of DDFP-Compound 20a nanoemulsion exceeds the initial values obtained for nanoemulsion of DDFP-compound 21, TDFH-compound 21 and TDFH-Compound 20a, but are still within the release and shelf-life specification discussed for nanoemulsion described herein.

Figure 7:
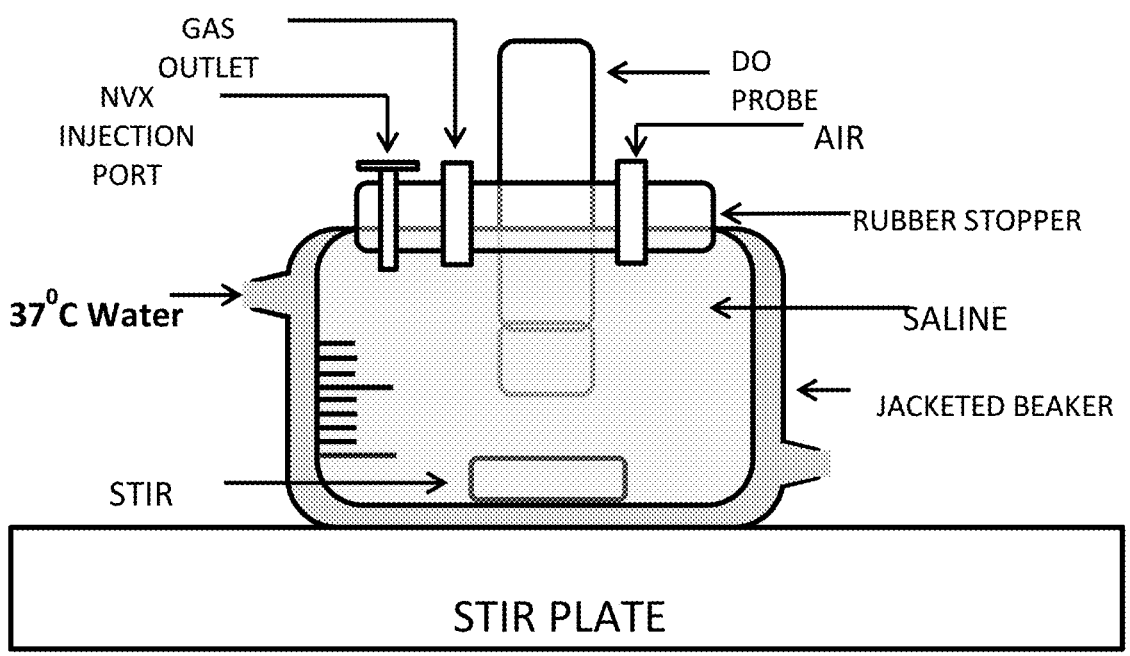
FIG. 7 is a diagram of an exemplary apparatus that measures uptake of dissolved oxygen from a solution before and after addition of a test solution of a nanoemulsion of perfluorocarbon and surfactant.
Figure 8:
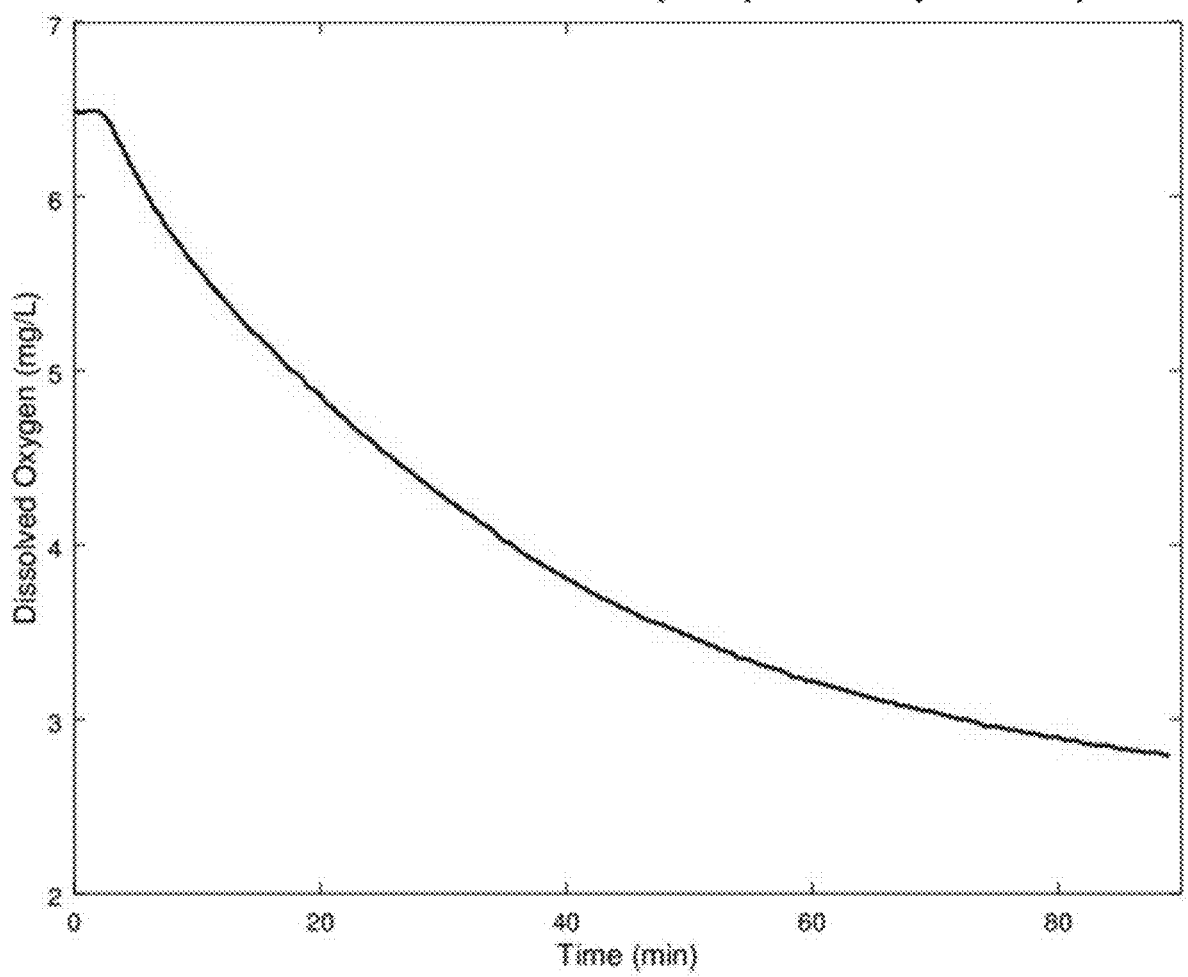
FIG. 8 is a graph of dissolved oxygen content of an aqueous solution prior to and after addition of the perfluorocarbon nanoemulsion of Example 5.

The formulation is designed to imbibe oxygen into the perfluorocarbon in oxygen rich regions and to release oxygen upon transport to tissues where there is an oxygen deficit resulting in low oxygen tension (hypoxic tissue). Hence when the formulation is injected into an oxygen-rich environment or an environment wherein the oxygen concentration is higher than that in the emulsified perfluorocarbon, it first imbibes dissolved oxygen from the solution in which it is present. When the nanoemulsion particles are transported to hypoxic tissues, or tissues wherein the dissolved oxygen concentration is lower than that in the nanoparticles, oxygen is released from the nanoparticles as expected based on the physical gradient of oxygen concentration. To evaluate whether the formulation of this example can imbibe oxygen from aqueous solution, in vitro testing was conducted using the setup shown in FIG. 7. A jacketed beaker containing approximately 200 mL of 0.9% saline along with a stir bar, was connected to a circulating water bath (Temp=37° C.±0.3° C.) and placed on a stir plate (Speed=550 RPM). The top of the beaker was covered using a rubber stopper that contained an access hole for an Oakton DO 110 dissolved oxygen probe (Vernon Hills, Ill.) and a smaller hole for the introduction of the formulation. After the temperature and dissolved oxygen readings equilibrated, 5 mL of the formulation was injected into the 0.9% saline solution through the small access hole. The access hole was then sealed using a luer plug fitting and the top of the vessel was wrapped in parafilm to prevent oxygen from entering the vessel. Dissolved oxygen readings were obtained for 90 minutes at 30 second intervals and transferred to a laptop computer automatically using the serial port connection on the dissolved oxygen meter and the vendor supplied CyberComm Portable data acquisition software. A clear decrease in oxygen level over the measurement period is shown in graphical form in FIG. 8. The corresponding graph using a saline control displayed no decrease in dissolved oxygen level over the same period.

Example 6

Use of C16-Based Phospholipid Surfactant System for Preparation of a Nanoemulsion of DDFP Experiments were conducted to study the submicron particle size of DDFP nanoemulsion prepared in a palmitoyl-based phospholipid surfactant system. A 22 mL aliquot of propylene glycol in a 50 mL beaker was heated to 55° C. with stirring. 1,2-Dipalmitoyl-sn-glycero-3-phosphatidylcholine (399 mg), 1,2-palmitoyl-sn-glycero-3-phosphoethanolamine-N-[methoxy(polyethylene glycol)-5000] sodium salt (305 mg), and 1,2-dipalmitoyl-sn-glycero-3-phosphoethanolamine (45.88 mg) were added sequentially with stirring and the mixture is stirred until the phospholipids dissolve (5-15 min). Then the propylene glycol solution of phospholipids was added dropwise over a period of about 2 min to a stirred mixture of water/glycerol 95/5 v/v (200.7 mL) containing monobasic sodium phosphate.$H_2O$ (173.9 mg) and anhydrous dibasic sodium phosphate (137.87 mg) at 55° C. The solution was stirred for 5 min after the addition of the glycerol solution of the phospholipids. The solution was immediately push-filtered through a 32 mm Pall Sciences GH Polypro® 0.2 micron filter into a 250 mL bottle which is then immediately purged with dry ultrapure nitrogen. The solution was allowed to cool to ambient temperature. Then nominal 5 mL serum vials (actual capacity 9 mL) were charged with a 7.56 mL aliquot of the phospholipid suspension followed by purging the headspace with dry ultrapure nitrogen and stoppering with halobutyl rubber stoppers. The stoppered vials (in trays) were placed in a refrigerator at 4° C. until the vial contents equilibrated to that temperature. Then the trays were removed and the vials were charged with DDFP (Fluoromed, Round Rock, Tex.) and crimp capped as described in Example 5. The nanoemulsion was prepared by vortexing the vial and sonication (for different time periods) as described in Example 5. The sonication periods were 2 min, 8 min, and 16 minutes.

TABLE 12

Submicron Particle Sizing of DDFP-DPPC-DPPE-DPPE-MPEG5000 Nanoemulsion Prepared by Vortexing and Sonication of Mixed Components

| Sample Processing | IWMD (nm) | Std. Dev. (nm) | % Std. Dev. | 99% of Dist < (nm) | $Chi^2$ | VWMD* (nm) | NWMD* (nm) |
|---|---|---|---|---|---|---|---|
| Vortex 1 min Sonicate 2 min | 396 | 163.8 | 41.41 | 950.7 | 0.11 | 451.8 | 201.3 |
| Vortex 1 min Sonicate 8 min | 372 | 139.7 | 37.51 | 830.1 | 0.12 | 414.2 | 222.3 |
| Vortex 1 min Sonicate 16 min | 360 | 103.7 | 28.81 | 674.6 | 0.58 | 386.9 | 286 |

*VWMD = Volume weighted mean diameter, NWMD = Number weighted mean diameter

According to the data in Table 12, the nanoemulsion obtained after 16 minutes of sonication is within the optimum value for intensity weighted mean particle diameter and the 99% Cumulative distribution<value is comparable to the desired value for DDFP nanoemulsion using perfluorocarbon-based surfactant systems.

Example 7

Preparation of DDFP Nanoemulsion Using a C14-Based Phospholipid System as Surfactant and Sonication of Vials of the Mixed Components A 22 mL aliquot of propylene glycol in a 50 mL beaker was heated to 55° C. with stirring. 1,2-Dimyristoyl-sn-glycero-3-phosphatidylcholine (677.9 mg), 1,2-dimyristoyl-sn-glycero-3-phosphoethanolamine-N-[methoxy(polyethylene glycol)-2000] sodium salt (174 mg), and 1,2-dimyristoyl-sn-glycero-3-phosphoethanolamine (50.95 mg) were added sequentially with stirring and the mixture was stirred until the phospholipids dissolve (~15 min). Then the propylene glycol solution of phospholipids was added dropwise over a period of about 2 min into a stirred mixture of water/glycerol 95/5 v/v (200.7 mL) containing monobasic sodium phosphate.$H_2O$ (173.9 mg) and anhydrous dibasic sodium phosphate (137.87 mg) at 55° C. The solution was stirred for 5 min after the addition of the glycerol solution of the phospholipids. The solution was immediately push-filtered through a 32 mm Pall Sciences GH Polypro® 0.2 micron filter into a 250 mL bottle which was then immediately purged with nitrogen. The solution was allowed to cool to ambient temperature. Then nominal 5 mL serum vials (actual capacity 9 mL) were charged with a 7.56 mL aliquot of the phospholipid suspension followed by purging the headspace with dry ultrapure nitrogen and stoppered with halobutyl rubber stoppers. The stoppered vials (in trays) were placed in a refrigerator at 4° C. until the vial contents had equilibrated to that temperature. Then the trays were removed and the vials were charged with DDFP (Fluoromed, Round Rock, Tex.) and crimp capped as described in Example 5. The nanoemulsion was prepared by vortexing the vial and sonication as described in Example 5.

TABLE 13

Submicron Particle Sizing Data for DDFP-Phospholipids-30% Buffered Sucrose formulation of Example 7

| IWMD (nm) | VWMD (nm) | NWMD (nm) | Standard Deviation (%) | $Xi^2$ | IW99% CUM < (nm) | VW99% CUM < nm |
|---|---|---|---|---|---|---|
| 301.6 | 313.6 | 240.7 | 25.9 | 0.22 | 532.4 | 553.7 |

Figure 9:
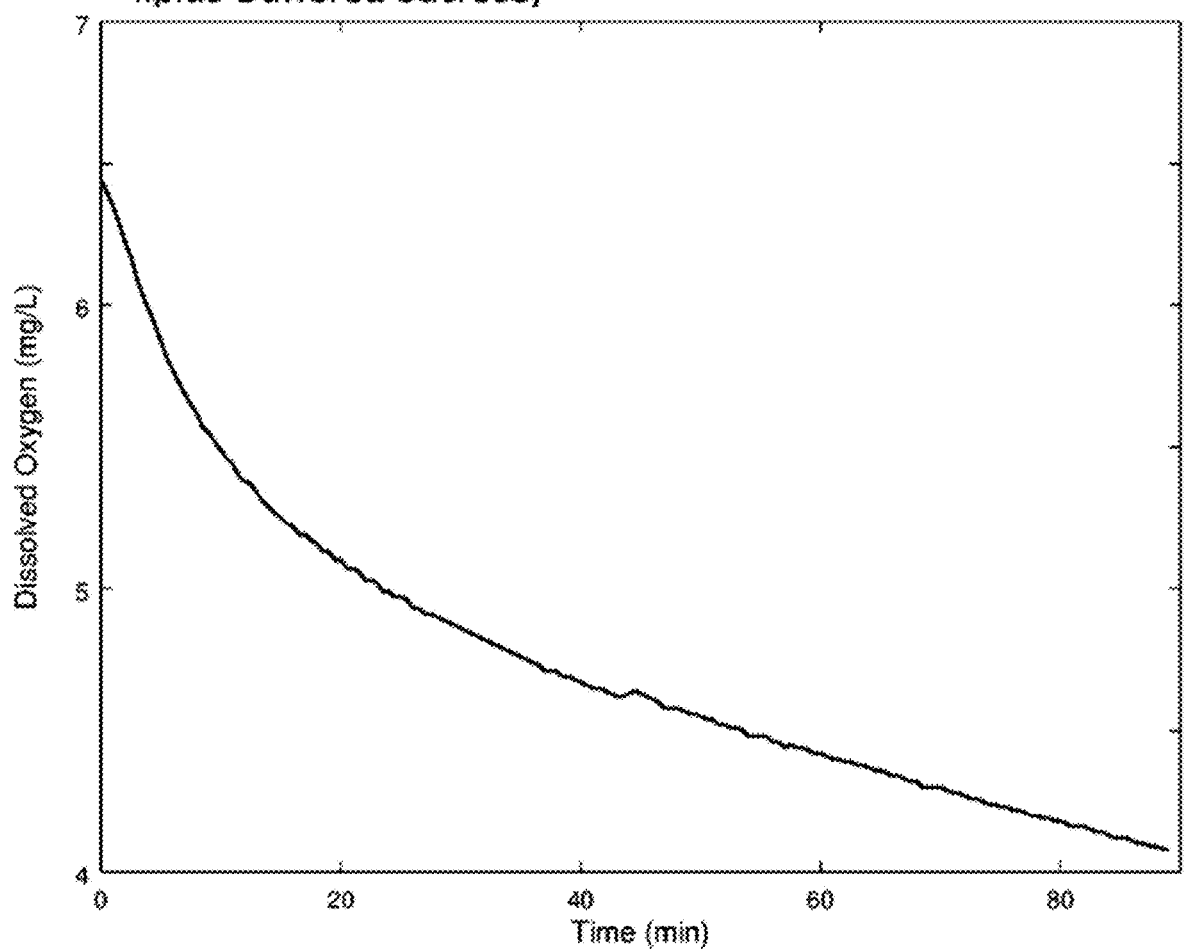
FIG. 9 is a graph showing decrease in dissolved oxygen level in aqueous solution post addition of the formulation of Example 7.

The formulation was evaluated for its ability to imbibe oxygen from an oxygen rich environment as described for the evaluation of the formulation of Example 5. A clear decrease in oxygen level over the measurement period is shown in graphical form in FIG. 9. The corresponding graph using a saline control displayed no decrease in dissolved oxygen level over the same period.

Example 8

Preparation of DDFP Nanoemulsion using a C14-based phospholipid system combined with Compound 20a (DuPont FS-3100) as surfactant and sonication of vials of the mixed components.

A formulation of 1,2-Dimyristoyl-sn-glycero-3-phosphatidylcholine (677.9 mg), 1,2-dimyristoyl-sn-glycero-3-phosphoethanolamine-N-[methoxy(polyethylene glycol)-2000] sodium salt (174 mg), and 1,2-dimyristoyl-sn-glycero-3-phosphoethanolamine (50.95 mg) and neat DuPont Capstone FS-3100 compound 20a, (16 µL, 23 mg, 0.3% w/v) followed by DDFP (0.153 g, 89 µL, 2% w/v). The vial was immediately vortexed for 1 minute upright and 1 minute inverted. Then the vial was sonicated for 8 min in a VWR Aquasonic 75HT ultrasonic cleaning bath for 8 minutes. Following this a 5.2 mL aliquot of the emulsion was removed from the vial and a 0.1 mL aliquot subjected to particle sizing using the PSS Nicomp 380 DLS submicron particle sizer and a 5 mL aliquot employed in the oxygen uptake assay described above. The particle sizing data for this formulation post sonication is shown in Table 14.

TABLE 14

Submicron Particle Sizing Data for DDFP-Capstone FS-3100-Phospholipids-30% Buffered Sucrose formulation of Example 7

| IWMD (nm) | VWMD (nm) | NWMD (nm) | Standard Deviation (%) | $Xi^2$ | IW99% CUM < (nm) | VW99% CUM < nm |
|---|---|---|---|---|---|---|
| 204.1 | 171.1 | 105.1 | 34.9 | 0.25 | 432.3 | 363.7 |

Figure 10:
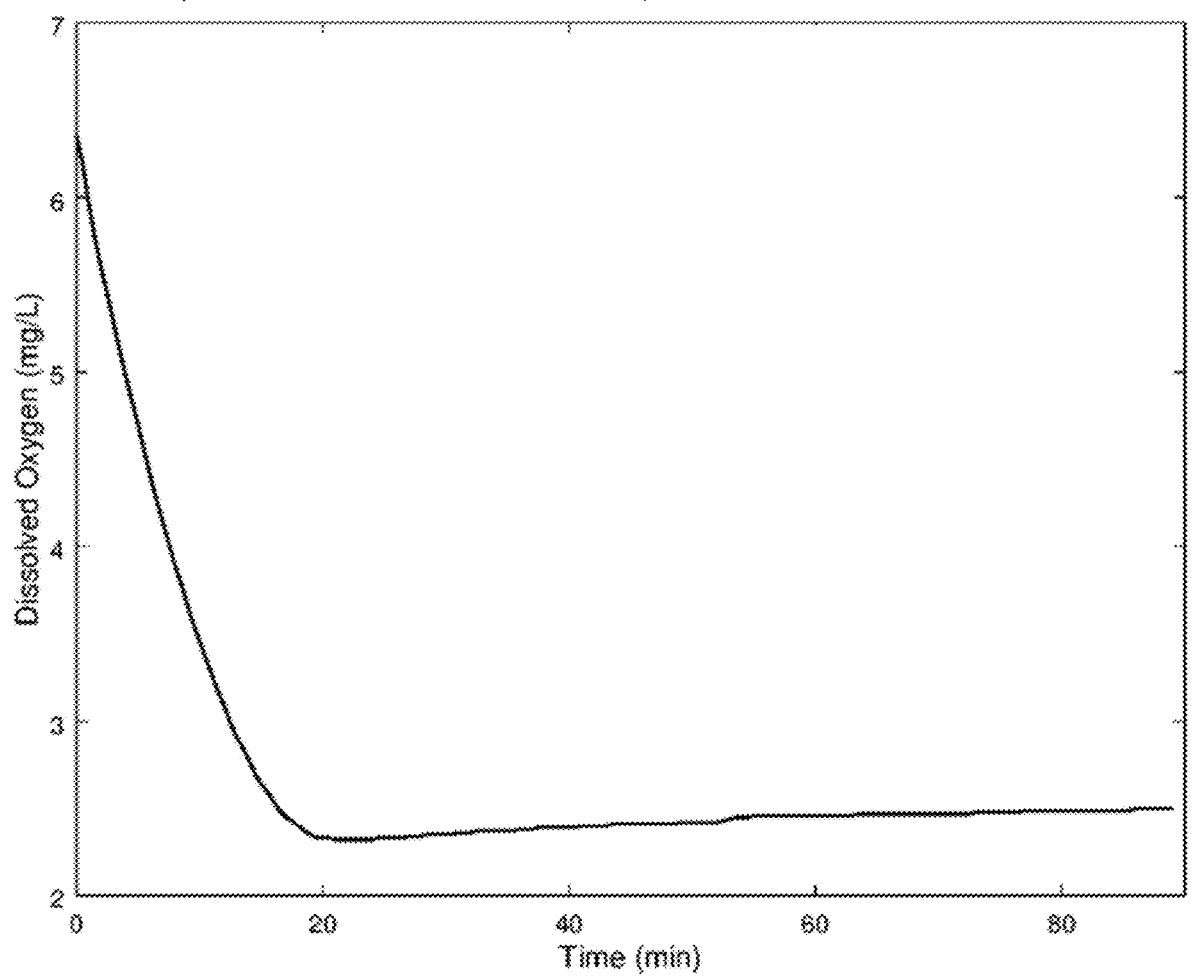
FIG. 10 is a graph showing decrease in dissolved oxygen level in aqueous solution post addition of the formulation of Example 8.

A clear decrease in oxygen level over the measurement period is shown in graphical form in FIG. 10. The corresponding graph using a saline control displayed no decrease in dissolved oxygen level over the same period.

Prophetic Example 1

Preparation of DDFP Nanoemulsion Using a C14-Based Phospholipid System as Surfactant and Homogenization of the Primary Emulsion Followed by Homogenization Transfer and Submicron Filtration A 22 mL aliquot of propylene glycol in a 50 mL beaker is heated to 55° C. with stirring. 1,2-Dimyristoyl-sn-glycero-3-phosphatidylcholine (677.9 mg), 1,2-dimyristoyl-sn-glycero-3-phosphoethanolamine-N-[methoxy(polyethylene glycol)-2000] sodium salt (174 mg), and 1,2-dimyristoyl-sn-glycero-3-phosphoethanolamine (50.95 mg) are added sequentially with stirring and the mixture is stirred until the phospholipids dissolve (~15 min). The solution is allowed to cool to ambient temperature followed by addition of water for injection (20 mL) cooling to 10° C. and addition of cold DDFP (4.51 g, 2.61 mL) and stirring rapidly for 30 min at 10° C. The resulting material is subjected to discrete homogenization using a Kirkland products hand held homogenizer at 5° C. for a total of 20 passes. This material is then added to a solution of glycerol in water for injection. Then the nanoemulsion is added to a stirred solution of 205.4 mL of 30% sucrose and stirred for 10 min under a nitrogen atmosphere (5 psi). After this the solution is transferred via the homogenizer to a second vessel kept at 2-5° C. after which it is stirred for 15 minutes and filtered through a Pall Sciences 0.8/0.2 micron Acropak 200 filter into a third vessel at 2-5° C. and stirred for 15 minutes at that temperature after transfer. The material is then filled into nominal 5 mL Wheaton vials, stoppered with gray halobutyl rubber stoppers and crimp capped and stored.

Prophetic Example 2

Formation of TDFH Nanoemulsion Using a C14-Based Phospholipid System as Surfactant A 22 mL aliquot of propylene glycol in a 50 mL beaker is heated to 55° C. with stirring. The phospholipids of Example 1 are added with stirring and the mixture is stirred until the phospholipids dissolve (~15 min). Then the propylene glycol solution of phospholipids is added dropwise over a period of about 2 min to a stirred mixture of water/glycerol 95/5 v/v (200.7 mL) containing monobasic sodium phosphate.$H_2O$ (173.9 mg) and anhydrous dibasic sodium phosphate (137.87 mg) at 55° C. The solution is stirred for 5 min after the addition of the glycerol solution of the phospholipids. The solution is immediately push-filtered through a 32 mm Pall Sciences GH Polypro® 0.2 micron filter into a 250 mL bottle which is then immediately purged with nitrogen. The solution is allowed to cool to ambient temperature. Then nominal 5 mL serum vials (actual capacity 9 mL) are charged with a 7.56 mL aliquot of the phospholipid suspension followed by purging the headspace with dry ultrapure nitrogen and stoppering with halobutyl rubber stoppers. The stoppered vials (in trays) are placed in a refrigerator at 4° C. until the vial contents have equilibrated to that temperature. Then the trays are removed and the vials are charged with TDFH (Sigma Aldrich Co. St. Louis, Mo.) and crimp capped as described in Example 5. The nanoemulsion is prepared by vortexing the vial and sonication as described in Example 5.

Prophetic Example 3

Preparation of DDFP Nanoemulsion Using a C14-Based Phospholipid System with Compound 20a as Co-Surfactant and Sonication of Vials of the Mixed Components The methods of Example 6 are followed except that the surfactant system comprises 30 mole percent compound 20a in addition to the C14-phospholipid-based system. The nano-emulsion is then prepared similarly. Similar procedures and techniques from Examples 1-6 and prophetic Examples 1 and 2 can be employed for preparation of nanoemulsions based on lauroyl (C12)-based phospholipid surfactant systems.

While the preferred embodiments of the present invention have been illustrated in detail, it should be apparent that modifications and adaptations to those embodiments may occur to one skilled in the art without departing from the scope of the present invention.

Prophetic Example 4

Preparation of DDFP Nanoemulsion Using a C12-Based Phospholipid System as Surfactant and Homogenization of the Primary Emulsion Followed by Homogenization Transfer and Submicron Filtration A 22 mL aliquot of propylene glycol in a 50 mL beaker is heated to 55° C. with stirring. 1,2-didodecanoyl-sn-glycero-3-phosphatidylcholine (677.9 mg), 1,2-didodecanoyl-sn-glycero-3-phosphoethanolamine-N-[methoxy(polyethylene glycol)-2000] sodium salt (174 mg), and 1,2-didodecanoyl-sn-glycero-3-phosphoethanolamine (50.95 mg) are added sequentially with stirring and the mixture is stirred until the phospholipids dissolve (~15 min). The solution is allowed to cool to ambient temperature followed by addition of water for injection (20 mL) cooling to 10° C. and addition of cold DDFP (4.51 g, 2.61 mL) and stirring rapidly for 30 min at 10° C. The resulting material is subjected to homogenization using a Kirkland products hand held homogenizer at 5° C. for a total of 20 passes. This material is then added to a solution of glycerol in water for injection. Then the nanoemulsion is added to a stirred solution of 205.4 mL of 30% sucrose and stirred for 10 min under a nitrogen atmosphere (5 psi). After this the solution is transferred via the homogenizer to a second vessel kept at 2-5° C. after which it is stirred for 15 minutes and filtered through a Pall Sciences 0.8/0.2 micron Acropak 200 filter into a third vessel at 2-5° C. and stirred for 15 minutes at that temperature after transfer. The material is then filled into nominal 5 mL Wheaton vials, stoppered with gray halobutyl rubber stoppers and crimp capped and stored.

Applicants' disclosure is described herein in preferred embodiments with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicants' disclosure may be combined in any suitable manner in one or more embodiments. In the description herein, numerous specific details are recited to provide a thorough understanding of embodiments of the invention. One skilled in the relevant art will recognize, however, that Applicants' composition and/or method may be practiced without one or more of the specific details, or with other methods, components, materials, and so forth. In other instances, well-known structures, materials, or operations are not shown or described in detail to avoid obscuring aspects of the disclosure.

The schematic flow chart diagrams included are generally set forth as logical flow-chart diagrams (e.g., FIGS. 1, 2, 3, 4, and 5). As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow-chart diagrams, they are understood not to limit the scope of the corresponding method (e.g., FIGS. 1, 2, 3, 4, and 5). Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof

The invention claimed is:

1. A composition of a fluorocarbon nanoemulsion comprising:
   perfluorohexane; and
   one or more surfactants selected from perfluoro-n-hexyl-oligoethyleneoxy-alcohols,
   wherein the nanoemulsion is characterized by:
   perfluorohexane accounting for a weight percent in the nanoemulsion from about 1% to about 10%,
   the perfluoro-n-hexyl-oligoethyleneoxy-alcohol accounting for a weight percent in the nanoemulsion from about 0.10% to about 7.5%,
   a particle distribution wherein 99% of the particles are measured to have particle diameters of less than or equal to 400 nm, and
   the perfluoro-n-hexyl-oligoethyleneoxy-alcohol is selected from the group consisting of:

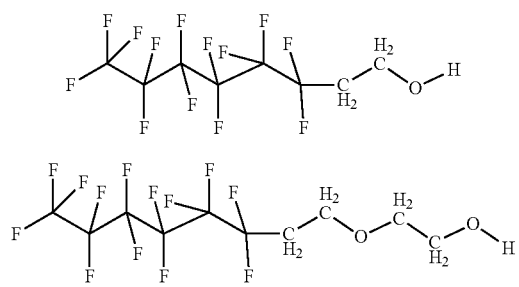

2. The composition of claim 1, wherein the perfluoro-n-hexyl-oligoethyleneoxy-alcohol accounts for a weight percent in the nanoemulsion from about 0.10% to about 1.5%.

3. A composition of a fluorocarbon nanoemulsion comprising:
   perfluorohexane; and
   a perfluoro-n-hexyl-oligoethyleneoxy-alcohol as a surfactant,
   wherein the nanoemulsion is characterized by:
   perfluorohexane accounting for a weight percent in the nanoemulsion from about 1% to about 10%,
   the perfluoro-n-hexyl-oligoethyleneoxy-alcohol accounting for a weight percent in the nanoemulsion from about 0.10% to about 7.5%,
   a particle distribution wherein 99% of the particles are measured to have particle diameters of less than or equal to 400 nm, and
   the perfluoro-n-hexyl-oligoethyleneoxy-alcohol is selected from the group consisting of:

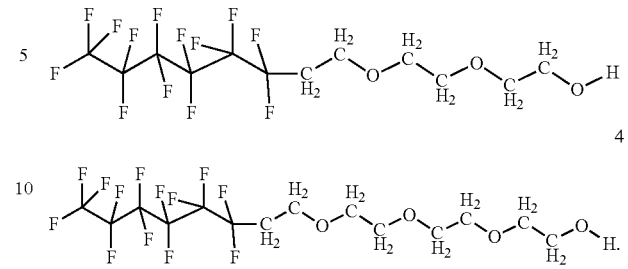

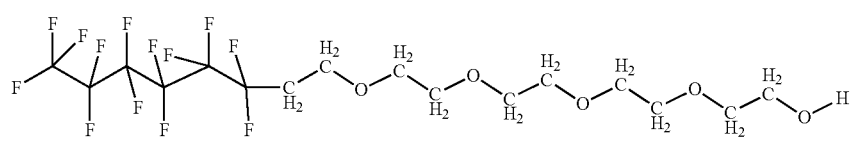

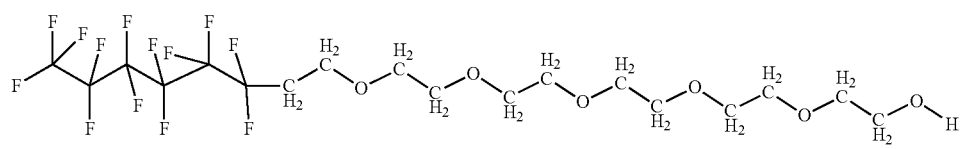

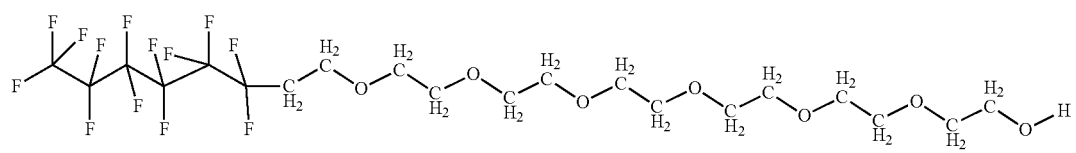

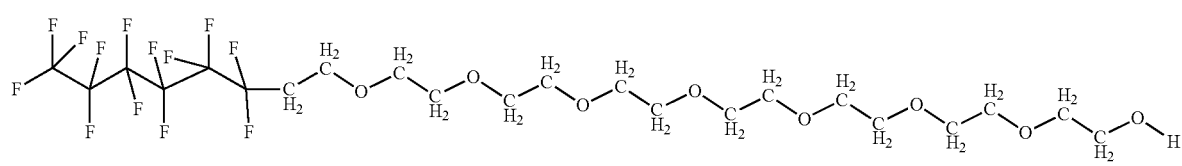

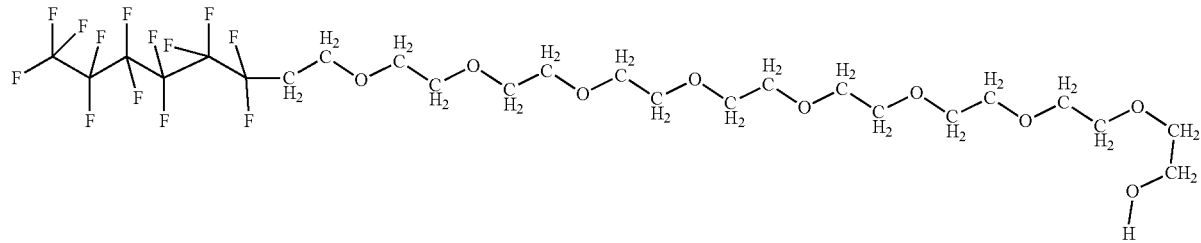
9
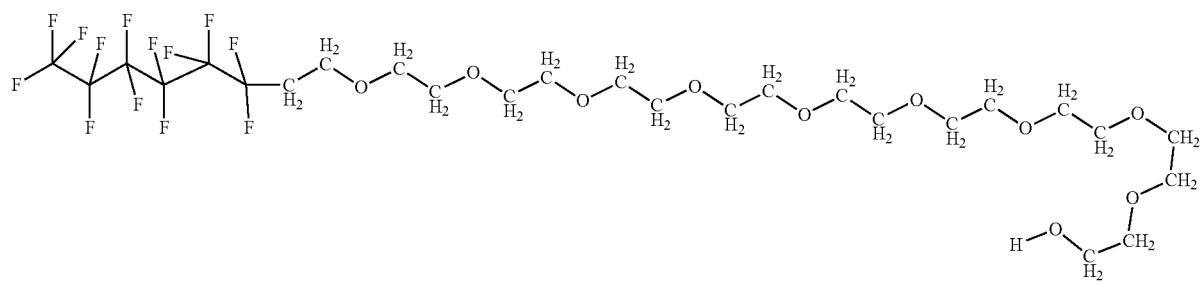
10
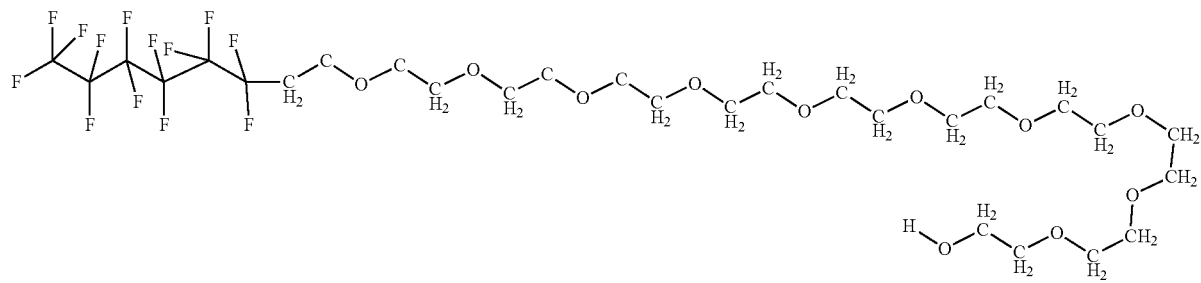
11
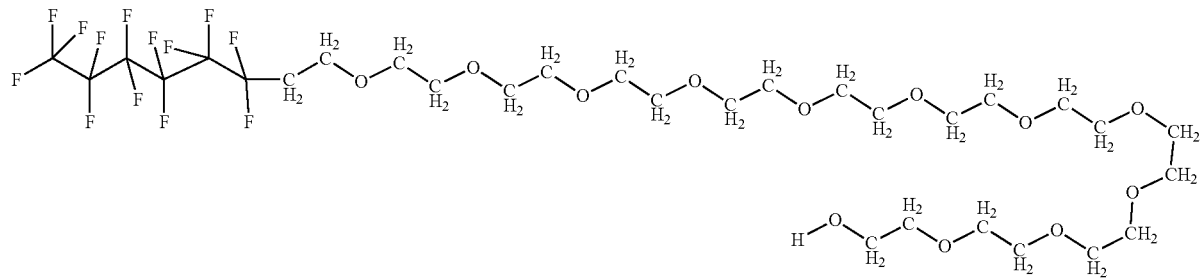
12
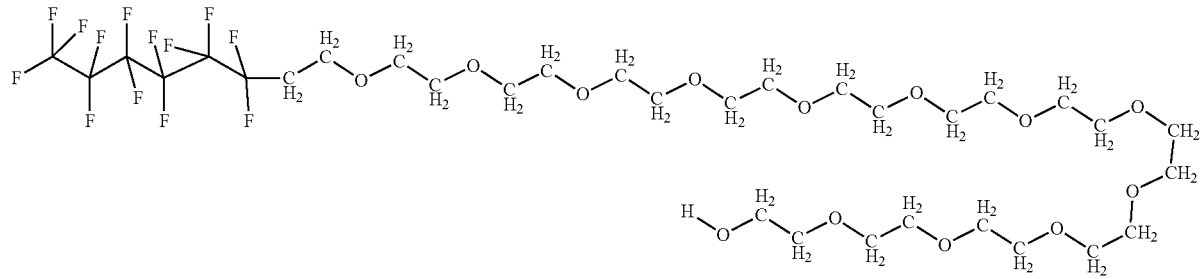
13

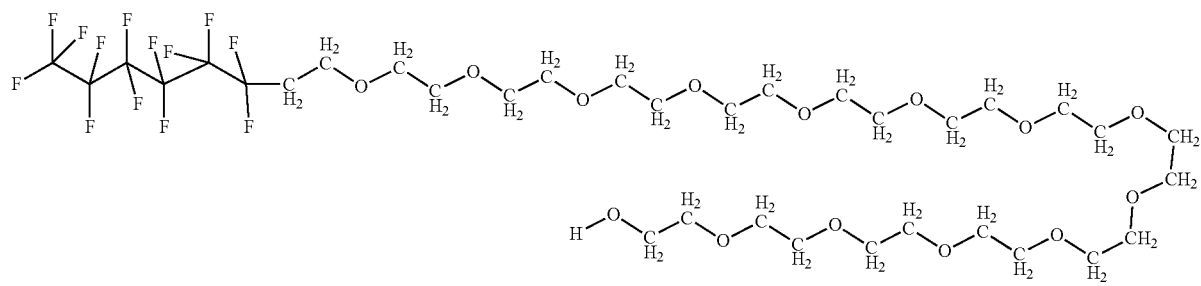
14
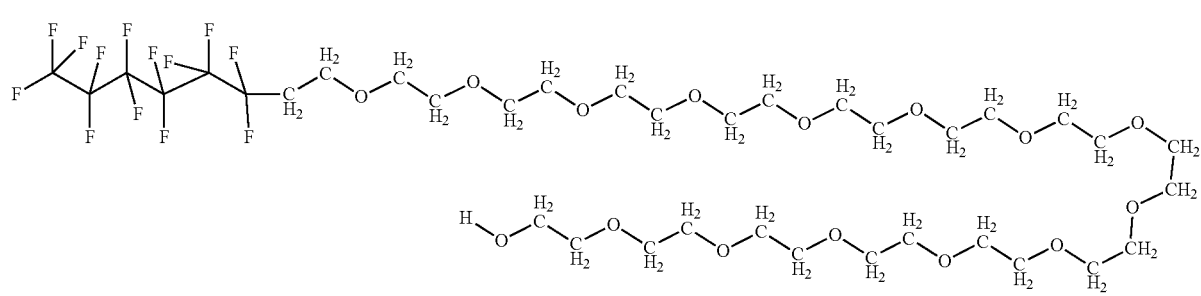
15
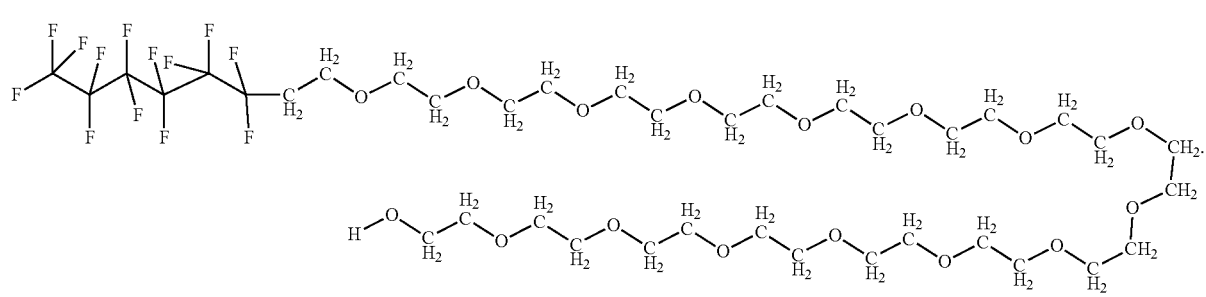
16
4. The composition of claim 3, wherein the perfluoro-n-hexyl-oligoethyleneoxy-alcohol accounts for a weight percent in the nanoemulsion from about 0.10% to about 1.5%.
* * * * *